(12) United States Patent
Knight et al.

(10) Patent No.: US 11,931,084 B2
(45) Date of Patent: Mar. 19, 2024

(54) METHOD AND APPARATUS FOR AN ORTHOPEDIC FIXATION SYSTEM

(71) Applicant: DEPUY SYNTHES PRODUCTS, INC., Raynham, MA (US)

(72) Inventors: Adam T. Knight, Douglassville, PA (US); Daniel F. Cheney, Downingtown, PA (US); Lisa P. Actis, Honey Brook, PA (US); Donald W. Petersen, Helotes, TX (US)

(73) Assignee: DePuy Synthes Products, Inc., Raynham, MA (US)

(*) Notice: Subject to any disclaimer, the term of this patent is extended or adjusted under 35 U.S.C. 154(b) by 113 days.

(21) Appl. No.: 17/544,635

(22) Filed: Dec. 7, 2021

(65) Prior Publication Data

US 2023/0172647 A1 Jun. 8, 2023

(51) Int. Cl.
*A61B 17/86* (2006.01)
*A61B 17/00* (2006.01)

(52) U.S. Cl.
CPC ............ *A61B 17/8605* (2013.01); *A61B 2017/00867* (2013.01)

(58) Field of Classification Search
CPC ............ A61B 17/8605; A61B 17/8038; A61B 17/8042; A61B 17/8047; A61B 2017/00867
See application file for complete search history.

(56) References Cited

U.S. PATENT DOCUMENTS

| | | | |
|---|---|---|---|
| 9,005,251 B2 | 4/2015 | Heggeness | |
| 9,883,897 B2 | 2/2018 | Taber | |
| 10,064,619 B2 | 9/2018 | Palmer et al. | |
| 10,123,831 B2 | 11/2018 | Gephart | |
| 2011/0288590 A1* | 11/2011 | O'Farrell | A61B 17/7059 606/279 |
| 2012/0179208 A1* | 7/2012 | Geissler | A61B 17/8042 606/282 |
| 2013/0053895 A1* | 2/2013 | Stoll | A61B 17/8042 606/279 |
| 2015/0289910 A1* | 10/2015 | Mirghasemi | A61B 17/8014 606/71 |
| 2016/0089190 A1* | 3/2016 | Taber | A61B 17/80 606/281 |

(Continued)

FOREIGN PATENT DOCUMENTS

| | | |
|---|---|---|
| CN | 108078619 A | 5/2018 |
| WO | 2016025162 A1 | 2/2016 |

*Primary Examiner* — Kevin T Truong
*Assistant Examiner* — Diana Jones
(74) *Attorney, Agent, or Firm* — Christopher L. Makay

(57) ABSTRACT

An orthopedic fixation system includes an orthopedic implant and an implant retainer. The orthopedic implant includes a transition section deformable to move the orthopedic implant between a natural shape and an insertion shape whereby a transition of the orthopedic implant from the natural shape to the insertion shape stores deliverable energy and a transition of the orthopedic implant from the insertion shape to the natural shape delivers stored energy. The implant retainer is configured to mechanically engage the orthopedic implant across the transition section such the implant retainer constrains the orthopedic implant in the insertion shape thereby preventing a transition of the orthopedic implant from the insertion shape to the natural shape.

23 Claims, 24 Drawing Sheets

(56) References Cited

U.S. PATENT DOCUMENTS

2016/0268285 A1* 9/2016 Okamoto .............. H01L 27/092
2018/0214191 A1* 8/2018 Seo .................... A61B 17/8061
2019/0209215 A1* 7/2019 Baynham ........... A61B 17/8042
2019/0380754 A1* 12/2019 Wiederkehr ........... A61B 17/74

* cited by examiner

METHOD AND APPARATUS FOR AN ORTHOPEDIC FIXATION SYSTEM

BACKGROUND OF THE INVENTION

1. Field of the Invention

The present invention relates generally to orthopedic fixation and, more particularly, but not way of limitation, to an orthopedic fixation system including a shape memory implant and an implant retainer.

2. Description of the Related Art

Shape memory implants are commonly used in surgical procedures that require the reattachment or fusing of tissue or bone. Shape memory implants can be composed of a shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic (recoverable) deformation, and then releases the stored mechanical energy when the constraining instrument is removed. In these types of implants, the implants are mechanically deformed into their second shape and maintained in their second shape by instrumentation such that, upon release from the instrumentation, the implants elastically return to their first final shape from their second shape. Although thermally activated shape memory implants may be used without a constraining instrument, thermally activated shape memory implants often include a mechanical constraint in order to prevent premature activation prior to implantation in the event of exposure to a heat source.

In surgical procedures, the elastic or thermal properties of constrained shape memory implants are used as follows. Bones that require fixating are aligned, and the shape memory implant, which has been mechanically deformed to its second shape, is maintained in instrumentation and inserted across the bones. After insertion, the shape memory implant is released from the instrumentation, whereupon the shape memory implant elastically or upon heating tries to return to its first final shape such that the shape memory implant maintains the bones fixated together. The shape memory implant because it stores mechanical energy continuously applies force to the fixated bones as the shape memory implant tries to transition from the second shape to the first final shape, which aids in the healing process.

Various types of instrumentation can be used for either maintaining the shape memory implants in their second shape or moving an implant from its first final shape to a temporary second shape. Metal forceps are often employed to open and then insert the implant. These forceps have to be sterilized by a hospital, and then the implant can be placed on the forceps, opened to a desired position, and used for inserting the implant. Although potentially effective, forceps require the implant to be loaded into the forceps during surgery, which might be cumbersome and time consuming. In addition, forceps might be large and grip the implant at an underside thereof such that the forceps hinder implantation of the implant into a patient during surgery. It is also possible that a physician using the forceps might damage the implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Metal instrumentation alternative to forceps engage a shape memory implant at securing features thereof such as bone screw holes. This type of instrumentation allows preloading and sterilization of the implant with the implant already in the second shape, and, when the implant is elastic, the implant can be pre-activated so that it does not require heating with an external heater or body temperature after implantation. Although potentially effective, the instrumentation typically must be employed with an implant sufficiently large to include multiple securing features at each end unless the instrumentation releases the securing features of the implant prior to a complete engagement of the implant with bones, which may result in an improper delivery of the implant.

Other instrumentation includes plastic and disposable tools to maintain a shape memory implant in the second shape. This type of instrumentation can be preloaded and sterilized with the implant already in the second shape, and, when the implant is elastic, the implant can be pre-activated so that it does not require heating with an external heater or body temperature after use. One type of plastic and disposable instrument operates by having the implant fit inside a passage that is substantially the same diameter as the shape memory implant. By using this method, the instrumentation allows the shape memory implant to be preloaded prior to surgery. However, using instrumentation that substantially conforms to the profile of the shape memory implant can create several problems for a surgeon. First, this type of instrumentation often makes disengagement of the shape memory staple after implantation problematic. In particular, the shape memory implant sticks to the instrumentation due to the frictional engagement between the shape memory implant, which is trying to compress, and the passage of the instrumentation, resulting in a more difficult surgical procedure and the potential for a less than satisfactory fixation of tissue or bone. Second, this type of instrumentation results in an abrupt and sudden release of stored mechanical energy as the implant is removed from the device. This type of instrumentation accordingly provides no method of slowly transitioning the stored energy in the implant from the instrumentation to the bones being fixated. Finally, this type of instrumentation can result in entanglement during release, in which the implant begins to compress upon release thereby making extraction of this type of instrumentation more difficult.

Another type of plastic and disposable instrument includes arms movable between a disengaged position and an engaged position. The arms terminate in jaws such that, when the arms reside in their engaged position, the jaws contact the shape memory implant to maintain the shape memory implant open for insertion. While the movable arms and jaws release the implant without entanglement and further allow the slow transitioning of the implant, the jaws, due to their location when contacting the shape memory implant as well as their path of travel during removal from the shape memory implant, leave the implant situated above the bone surface such that tamping of the implant to a position flush with the bone surface is required. As a result, the instrument can be impractical for certain surgeries because it is not always possible to tamp and thus seat the implant flush with a bone surface after its release from the instrument, particularly when the implant includes anchoring members of limited length.

Accordingly, an instrument that constrains a shape memory implant in its second shape, allows the shape memory implant to be preloaded and sterilized prior to surgery, simplifies removal of the shape memory implant after implantation, and releases the shape memory implant at a bone surface thereby eliminating tamping would be beneficial.

SUMMARY OF THE INVENTION

In accordance with the present invention, an orthopedic fixation system includes an orthopedic implant and an implant retainer. The orthopedic implant is transitionable between a natural shape and an insertion shape whereby a transition of the orthopedic implant from the natural shape to the insertion shape stores deliverable energy and a transition of the orthopedic implant from the insertion shape to the natural shape delivers stored energy. The implant retainer is configured to mechanically engage the orthopedic implant such the implant retainer constrains the orthopedic implant in the insertion shape thereby preventing a transition of the orthopedic implant from the insertion shape to the natural shape.

The orthopedic implant includes a bridge, a first anchoring segment disposed at a first end of the bridge, a second anchoring segment disposed at a second end of the bridge, a transition section disposed in the bridge, a first aperture extending through the bridge, and a second aperture extending through the bridge. The transition section deforms to move the orthopedic implant between the natural shape and the insertion shape. The first aperture extends through the bridge adjacent the transition section at a first side thereof, whereas the second aperture extends through the bridge adjacent the transition section at a second side thereof. The first aperture and the second aperture, upon transition of the orthopedic implant from the natural shape to the insertion shape, are spaced apart across the transition section a distance.

The first anchoring segment includes a first opening extending through the bridge at the first end thereof adapted to receive a screw therethrough. The second anchoring segment includes a second opening extending through the bridge at the second end thereof adapted to receive a screw therethrough. The first anchoring segment may include a third opening extending through the bridge at the first end thereof exterior of the first opening. Similarly, the second anchoring segment may include a fourth opening extending through the bridge at the second end thereof exterior of the second opening. The third opening and the fourth opening are adapted to receive a screw therethrough.

The orthopedic implant may include a third anchoring segment disposed at the first end of the bridge adjacent the first anchoring segment. The third anchoring segment includes a third opening extending through the bridge at the first end thereof adjacent the first opening. The orthopedic implant may include a fourth anchoring segment disposed at the second end of the bridge adjacent the second anchoring segment. The fourth anchoring segment includes a fourth opening extending through the bridge at the second end thereof adjacent the second opening. The third opening and the fourth opening are adapted to receive a screw therethrough.

In an alternative, the first anchoring segment includes a first leg extending from the bridge at the first end thereof. Similarly, the second anchoring segment includes a second leg extending from the bridge at the second end thereof. The first anchoring segment may include a third leg extending from the bridge interior of the first leg. The second anchoring segment may include a fourth leg extending from the bridge interior of the second leg. The third anchoring segment in the alternative includes a third leg extending from the bridge at the first end thereof adjacent the first leg. Similarly, the fourth anchoring segment in the alternative includes a fourth leg extending from the bridge at the second end thereof adjacent the second leg.

The implant retainer includes a first fastener, a second fastener, and a retention block. The retention block includes a first hole therethrough adapted to receive the first fastener and a second hole therethrough adapted to receive the second fastener. The first hole and the second hole are spaced apart a distance equal to the distance between the first aperture of the bridge and the second aperture of the orthopedic implant when the orthopedic implant resides in the insertion shape. Upon transition of the orthopedic implant from the natural shape to the insertion shape, the retention block seats atop the bridge with the first hole of the retention block aligned with the first aperture of the bridge and the second hole of the retention block aligned with the second aperture of the bridge such that the retention block spans the transition section of the bridge. The first fastener inserts into the first hole of the retention block and extends into the first aperture, and the second fastener inserts into the second hole of the retention block and extends into the second aperture, thereby securing the retention block with the bridge across the transition section thereof. The retention block, in response to the securing thereof atop the bridge, constrains the bridge and holds the orthopedic implant in the insertion shape thereby preventing a transition of the orthopedic implant from the insertion shape to the natural shape.

The first aperture is configured for mechanical engagement with the first fastener thereby facilitating a rigid securing of the retention block with the bridge. Likewise, the second aperture is for mechanical engagement with the second fastener thereby facilitating a rigid securing of the retention block with the bridge. The first hole includes an upper segment with a counterbore configured to receive therein a head of the first fastener and a lower segment configured for mechanical engagement with a shaft of the first fastener. Similarly, the second hole includes an upper segment with a counterbore configured to receive therein a head of the second fastener and a lower segment configured for mechanical engagement with a shaft of the second fastener.

A method for an orthopedic fixation system includes transitioning an orthopedic implant about a transition section thereof from a natural shape to an insertion shape whereby the orthopedic implant stores deliverable energy such that a first aperture extending through the orthopedic implant adjacent the transition section at a first side thereof and a second aperture extending through the orthopedic implant adjacent the transition section at a second side thereof are spaced apart across the transition section a distance. The method further includes providing a retention block including a first hole and a second hole therethrough that are spaced apart a distance equal to the distance between the first aperture of the orthopedic implant and the second aperture of the orthopedic implant when the orthopedic implant resides in the insertion shape. The method then includes placing the retention block atop the orthopedic implant such that the retention block spans the transition section of the orthopedic implant, the first hole of the retention block aligns with the first aperture of the orthopedic implant, and the second hole of the retention block aligns with the second aperture of the orthopedic implant. The method next includes inserting a first fastener into the first hole of the retention block such that the first fastener extends into the first aperture of the orthopedic implant, and inserting a second fastener into the second hole of the retention block such that the second fastener extends into the second aperture of the orthopedic implant, thereby securing the retention block with the orthopedic implant across the transition section thereof. The method finally includes constraining the orthopedic implant with the retention block such that the retention block holds the orthopedic implant in the insertion shape thereby preventing a transition of the orthopedic implant from the insertion shape to the natural shape.

It is therefore an object of the present invention to provide an orthopedic fixation system with an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy.

It is another object of the present invention to provide an orthopedic fixation system with an implant retainer configured to mechanically engage the orthopedic implant such the implant retainer constrains the orthopedic implant in the insertion shape thereby preventing a transition of the orthopedic implant from the insertion shape to the natural shape.

It is a further object of the present invention to provide an orthopedic fixation system with an implant retainer that simplifies removal of an orthopedic implant therefrom and releases the orthopedic implant at a bone surface thereby eliminating tamping.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

Figure 1:
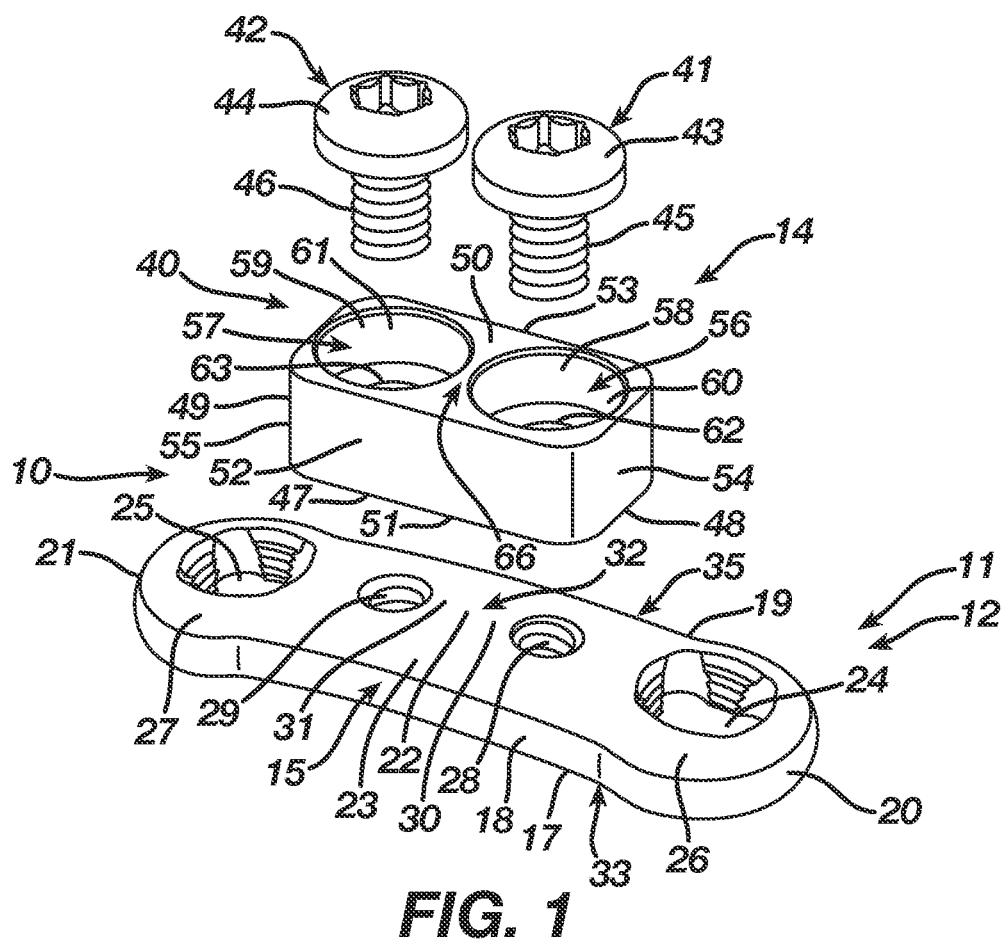
FIG. 1 is a top isometric view illustrating an orthopedic fixation system including an implant retainer disengaged from an orthopedic implant according to a first embodiment in a natural shape.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

An orthopedic fixation system 10 as illustrated in FIGS. 1 and 4A-4C includes an orthopedic implant 11 according to a first embodiment transitionable between a natural shape 12 and an insertion shape 13. The orthopedic fixation system 10 further includes an implant retainer 14 configured to engage the implant 11 and constrain the implant 11 in the insertion shape 13.

Figure 2A:
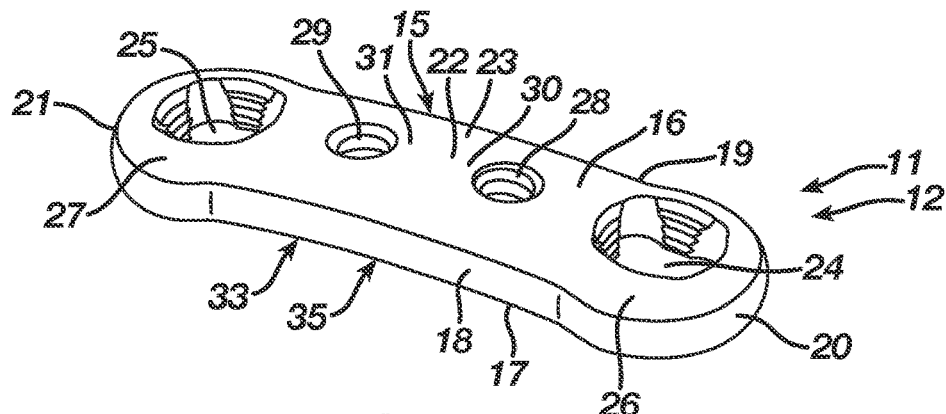
FIG. 2A is a top isometric view illustrating the orthopedic implant according to the first embodiment in the natural shape.
Figure 2B:
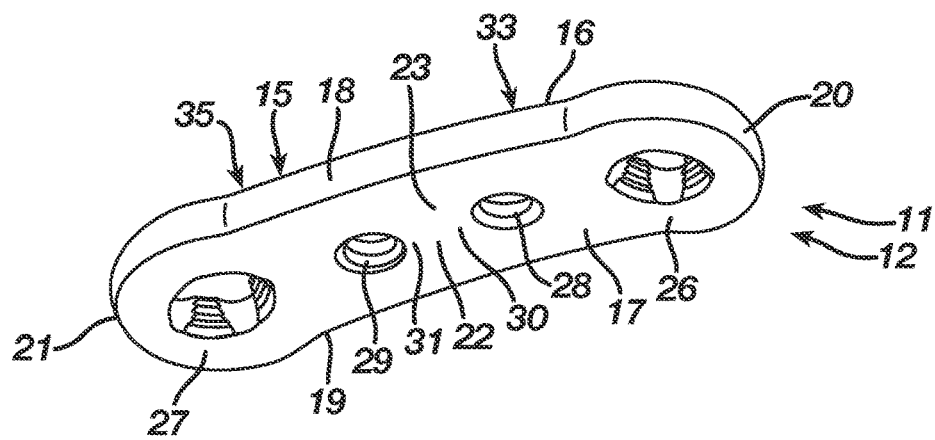
FIG. 2B is a bottom isometric view illustrating the orthopedic implant according to the first embodiment in the natural shape.
Figure 2C:
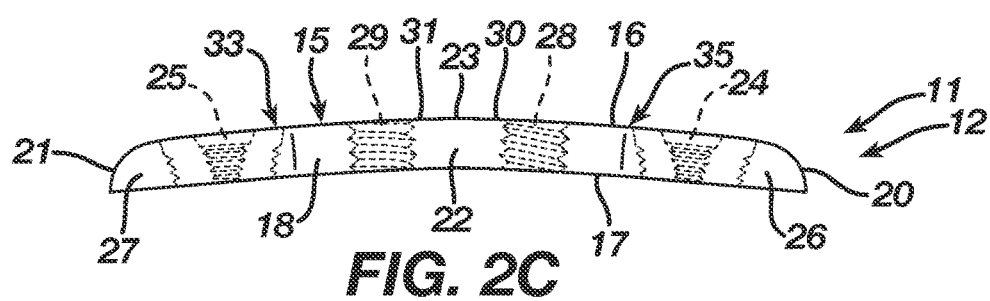
FIG. 2C is an elevation view illustrating the orthopedic implant according to the first embodiment in the natural shape.
Figure 2D:
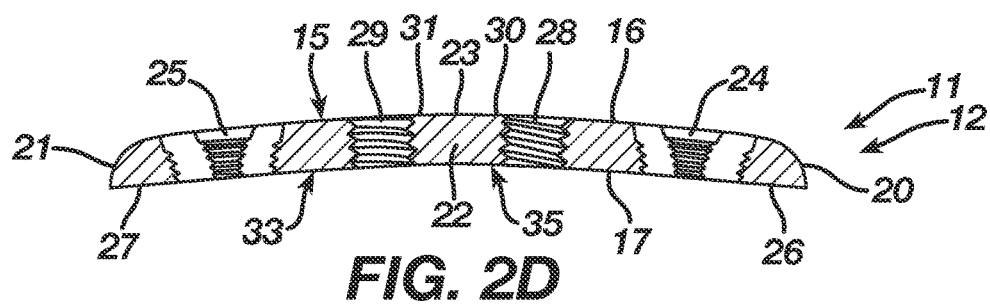
FIG. 2D is an elevation view in cross-section illustrating the orthopedic implant according to the first embodiment in the natural shape.
Figure 2E:
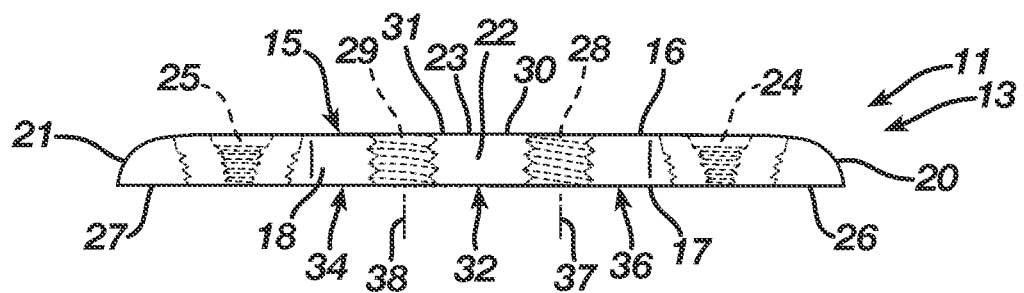
FIG. 2E is an elevation view illustrating the orthopedic implant according to the first embodiment in an insertion shape.
Figure 2F:
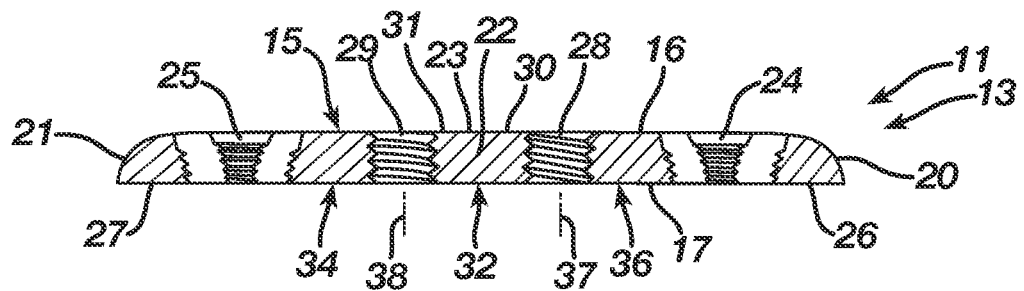
FIG. 2F is an elevation view in cross-section illustrating the orthopedic implant according to the first embodiment in the insertion shape.
Figure 3A:
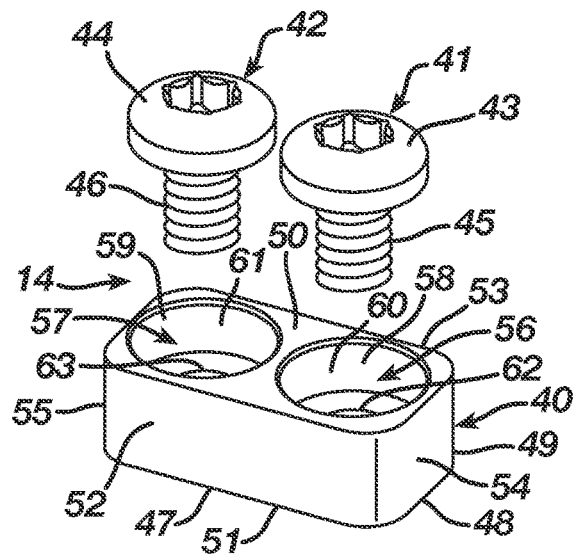
FIG. 3A is a top isometric view illustrating the implant retainer.
Figure 3B:
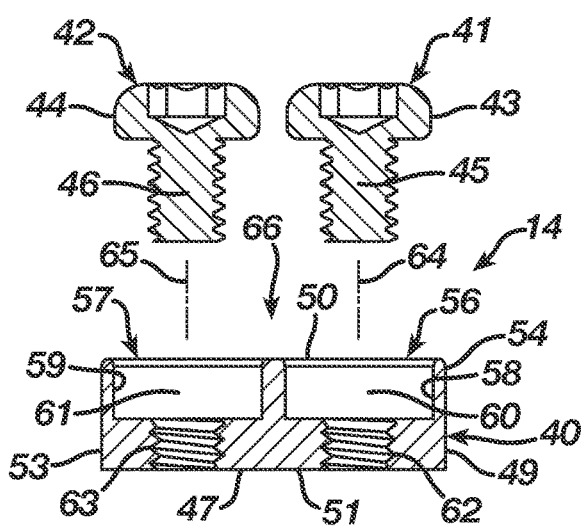
FIG. 3B is an elevation view in cross-section illustrating the implant retainer.
Figure 3C:
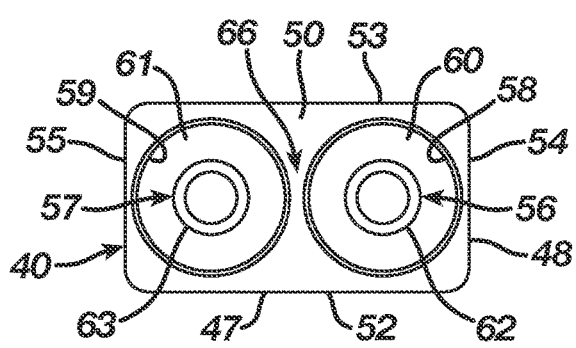
FIG. 3C is a top view illustrating the implant retainer.
Figure 3D:
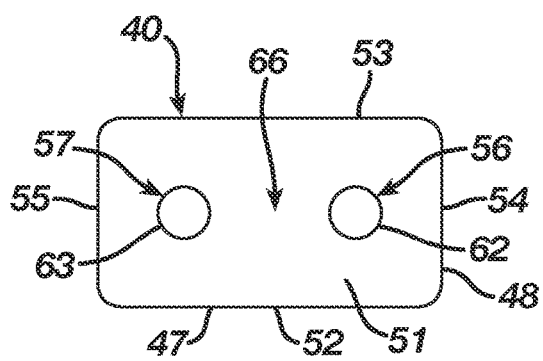
FIG. 3D is a bottom view illustrating the implant retainer.
Figure 4A:
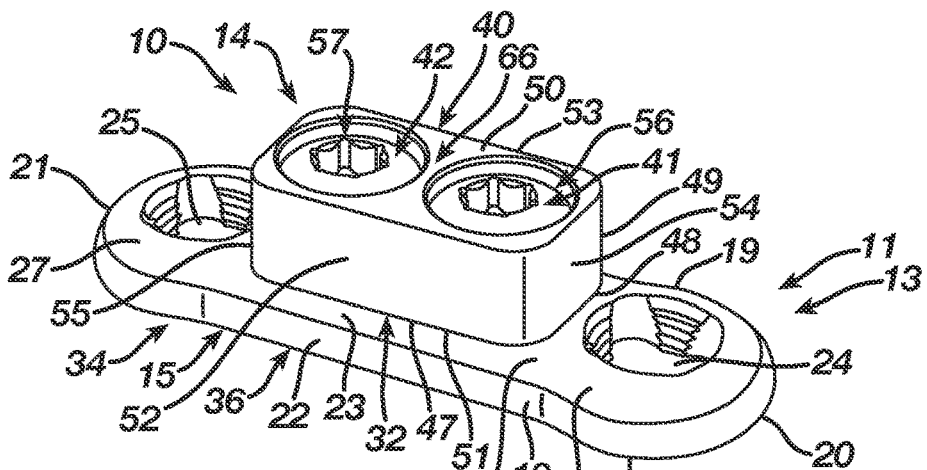
FIG. 4A is a top isometric view illustrating the orthopedic fixation system including the implant retainer engaged with the orthopedic implant according to the first embodiment in the insertion shape.
Figure 4B:
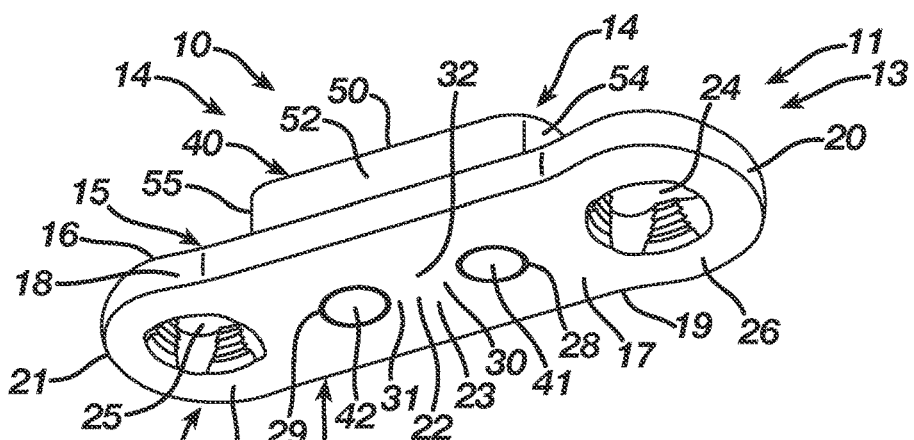
FIG. 4B is a bottom isometric view illustrating the orthopedic fixation system including the implant retainer engaged with the orthopedic implant according to the first embodiment in the insertion shape.
Figure 4C:
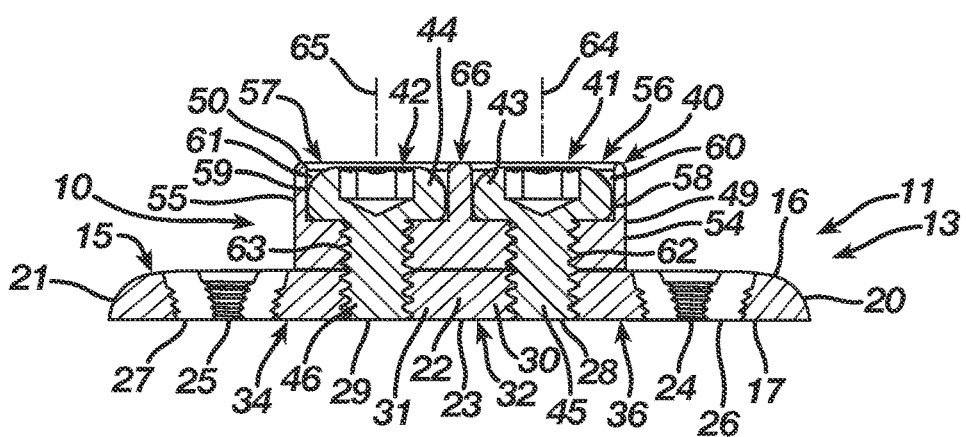
FIG. 4C is an elevation view in cross-section illustrating the orthopedic fixation system including the implant retainer engaged with the orthopedic implant according to the first embodiment in the insertion shape.

FIGS. 2A-2D illustrate the orthopedic implant 11 according to the first embodiment in the natural shape 12, whereas FIGS. 2E-2F illustrates the orthopedic implant 11 in the insertion shape 13. The implant 11 in the first embodiment may be manufactured from a shape memory material with superelastic or temperature dependent properties (e.g., Nitinol) such that the implant 11 transitions between the natural shape 12 and the insertion shape 13. The implant 11 when deformed from the natural shape 12 to the insertion shape 13 stores energy deliverable to bone, bones, or bone pieces. In accordance with its manufacture from shape memory material, the implant 11 begins in the natural shape 12, is transitionable to the insertion shape 13, and, once implanted in bone, bones, or bone pieces, attempts to transition from the insertion shape 13 to the natural shape 12 whereby the implant 11 delivers the energy stored therein to the bone, bones, or bone pieces in order to affix the bone, bones, or bone pieces and promote a healing thereof. In the first embodiment, attempted transition of the implant 11 from the insertion shape 13 to the natural shape 12 continuously compresses the bone, bones, or bone pieces to promote fusion thereof.

The implant 11 includes a bridge 15 with upper and lower surfaces 16 and 17, first and second sides 18 and 19, and first and second ends 20 and 21. The implant 11 includes a transition section 22 located at a center section 23 of the implant 11 and thus the bridge 15. The implant 11, and thus the bridge 15, includes a first opening 24 extending therethrough from the upper surface 16 to the lower surface 17 whereby the first opening 24 is located adjacent the first end 20 of the bridge 15 to provide the implant 11 and thus the bridge 15 with an anchoring segment 26. Likewise, the implant 11, and thus the bridge 15, includes a second opening 25 extending therethrough from the upper surface 16 to the lower surface 17 whereby the second opening 25 is located adjacent the second end 21 of the bridge 15 to provide the implant 11 and thus the bridge 15 with an anchoring segment 27. The first and second openings 24 and 25 receive anchoring members in the form of screws therethrough in order to facilitate a securing of the implant 11 at the first and second anchoring segments 26 and 27 with bone, bones, or bone pieces whereby the bridge 15 between the first and second openings 24 and 25 traverses a fixation zone of the bone, bones, or bone pieces. In accordance therewith, the implant 11, after its insertion and attempted transition from the insertion shape 13 to the natural shape 12, delivers energy to the bone, bones, or bone pieces at the fixation zone. Although the first and second openings 24 and 25 of the implant 11 primarily operate to receive therethrough anchoring members, the first and second openings 24 and 25 may receive therein respectively drill guides. The drill guides facilitate a drilling of holes in the bone, bones, or bone pieces that assist in inserting anchoring members through the first and second openings 24 and 25 and into the bone, bones, or bone pieces. The first and second openings 24 and 25 in the first embodiment include threads that facilitate engagement of the first and second openings 24 and 25 with anchoring members or the drill guides.

The implant 11, and thus the bridge 15, includes a first securing feature in the form of a first aperture 28, which is preferably threaded, extending therethrough from the upper surface 16 to the lower surface 17. The first aperture 28 preferably is located adjacent the transition section 22 at a first side 30 thereof. Similarly, the implant 11, and thus the bridge 15, includes a second securing feature in the form a second aperture 29, which is preferably threaded, extending therethrough from the upper surface 16 to the lower surface 17. The second aperture 29 preferably is located adjacent the transition section 22 at a second side 31 thereof. The first aperture 28 and the second aperture 29 provide engagement points for the implant retainer 14 with the implant 11. As such, the first aperture 28 at a vertical axis 36 and the second aperture 29 at a vertical axis 37, when the implant 11 resides in the insertion shape 13, are spaced apart across the transition section 22 a distance 32 that allows the first and second apertures 28 and 29 to facilitate a securing of the implant retainer 14 with the implant 11 at the transition section 22.

The regular inherent shape of the implant 11, as illustrated in FIGS. 2A-2D, is its natural shape 12 where the transition section 22 locates the bridge 15 in a natural form 33 consisting of a closed or angular profile whereby the first and second ends 20 and 21 reside at a first distance 35. Nevertheless, as illustrated in FIGS. 2E-2F, the implant 11 is deformable under the action of superelasticity or temperature dependent shape memory to its insertion shape 13 where the transition section 22 deforms to store energy while also moving the bridge 15 from its natural form 33 to an insertion form 34 which is an open or substantially linear profile whereby the first and second ends 20 and 21 reside at a second distance 36 that is greater than the first distance 35. Since the insertion shape 13 is not the regular inherent shape of the implant 11, the bridge 15 typically is mechanically constrained using the implant retainer 14 whereby the implant retainer 14 maintains the bridge 15 in its insertion form 34. In particular, the implant retainer 14, as described more fully herein, couples with the implant 11 via the first and second apertures 28 and 29, which are located at the distance 32 due to the implant 11 residing in the insertion shape 13, such that the implant retainer 14 holds the bridge 15 in the insertion form 34, resulting in the implant retainer 14 constraining the deformed transition section 22 in order to maintain the implant 11 in its insertion shape 13. After implantation into bone, bones, or bone pieces and a release of the implant retainer 14, including, if necessary, a heating of the implant 11, the implant 11 delivers the energy stored in the transition section 22 whereby the bridge 15 attempts to transition from its insertion form 34 to its natural form 33 such that the implant 11, which attempts transition from its insertion shape 13 to its natural shape 12, affixes the bone, bones, or bone pieces through an application of a compressive force thereto.

As illustrated in FIGS. 3A-3D, the implant retainer 14 includes a retention block 40 configured to receive first and second fasteners 41 and 42. The first fastener 41, which preferably is a screw, includes a head 43 and a shaft 45 with threads corresponding to the threads disposed in the first and second apertures 28 and 29 of the bridge 15 for the implant 11. Likewise, the second fastener 42, which preferably is a screw, includes a head 44 and a shaft 46 with threads corresponding to the threads disposed in the first and second apertures 28 and 29 of the bridge 15 for the implant 11. Although the first and second fasteners 41 and 42 and the first and second apertures 28 and 29 preferably employ threaded connections, one of ordinary skill in the art will recognize the first and second fasteners 41 and 42 and the first and second apertures 28 and 29 may be unthreaded and use only a friction fit.

The retention block 40 preferably is three-dimensional in form having a length 47, width 48, and height 49. More particularly, the retention block 40 is rectangular and includes an upper surface 50 and a lower surface 51 with first and second sides 52 and 53 and first and second ends 54 and 55 therebetween. The retention block 40 may be manufactured from any suitable rigid material, including but not limited to biocompatible metal or metal alloy, such as, for example, titanium, stainless steel, titanium alloy, and cobalt chrome alloy. While the retention block 40 is dimensionally configured to fit atop the bridge 15 of the implant 11 between the first and second sides 18 and 19 and the first and second openings 24 and 25 of the implant 11, the length 47, width 48, and height 49 of the retention block 40 are selected to provide the retention block 40 with a mechanical strength and rigidness sufficient to constrain the implant 11 in the insertion shape 13.

The retention block 40 includes first and second fastener receiving features in the form of first and second holes 56 and 57 extending therethrough from the upper surface 50 to the lower surface 51. The first hole 56 includes a counterbore 58 at an upper segment 60 thereof configured to receive therein either the head 43 of the first fastener 41 or the head 44 of the second fastener 42 and threads at a lower segment 62 thereof that correspond to the threads on either the shaft 45 of the first fastener 41 or the shaft 46 of the second fastener 42. The implant retainer 14 with respect to the retention block 40 and the first and second fasteners 41 and 42 and the implant 11 with respect to the first and second apertures 28 and 29 in the bridge 15 are correspondingly designed with respect to their size, location, and distances to interact and engage such that the implant retainer 14 optimally constrains the bridge 15 in its insertion form 34 and thus the implant 11 in its insertion shape 13. In accordance therewith, the first hole 56 at a vertical axis 64 and the second hole 57 at a vertical axis 65 reside a distance 66 equal to the distance 32 between the first and second apertures 28 and 29 of the bridge 15 for the implant 11 when the implant 11 resides in the insertion shape 13 such that, when the retention block 40 seats atop the bridge 15 residing in its insertion form 34, the retention block 40 spans the transition section 22 while the first hole 56 aligns with the first aperture 28 and the second hole 57 aligns with the second aperture 29 in order to facilitate an engagement of the retention block 40 with the bridge 15 across the transition section 22 using the first and second fasteners 41 and 42. Moreover, the height 49 of the retention block 40 is selected to provide the retention block 40 with a cross-sectional thickness that facilitates the head 43 of the first fastener 41 seating in the counterbore 58 while the shaft 45 extends through the lower segment 62 of the first hole 56 and into the first aperture 28 to a position whereby the shaft 45 resides at the lower surface 17 of the bridge 15 without protruding therefrom and the head 44 of the second fastener 42 seating in the counterbore 59 while the shaft 46 extends through the lower segment 63 of the second hole 57 and into the second aperture 29 to a position whereby the shaft 46 resides at the lower surface 17 of the bridge 15 without protruding therefrom. Although the first hole 56 and the second hole 57 have been described as aligning respectively with the first aperture 28 and the second aperture 29, one of ordinary skill in the art will recognize the orientation of the retention block 40 may be reversed in order for the first hole 56 to align with the second aperture 29 and the second hole 57 to align with the first aperture 28.

During formation of the orthopedic fixation system 10 through a securing of the implant retainer 14 with the implant 11 as illustrated in FIGS. 1 and 4A-4C, the implant 11 is mechanically deformed from the natural shape 12 to the insertion shape 13 such that the implant 11 stores mechanical energy. Mechanical deformation of the implant 11 may include cooling of the implant 11 whereby the implant 11 transitions from its austenite phase to its martensite phase in order to facilitate an easier mechanical deformation of the implant 11 from its natural shape 12 to its insertion shape 13 prior to a loading of the implant retainer 14 with the implant 11. Upon mechanical deformation of the implant 11 whereby the transition section 22 deforms to store energy while also moving the bridge 15 from its natural form 33 where the first and second ends 20 and 21 reside at the first distance 35 to its insertion form 34 where the first and second ends 20 and 21 reside at the second distance 36, the first aperture 28 and the second aperture 29 due to the movement of the bridge 15 now are spaced apart across the transition section 22 the distance 32. With the bridge 15 in its insertion form 34 and the first and second apertures 28 and 29 residing at the distance 32, the retention block 40 seats atop the bridge 15 at the upper surface 16 thereof in abutting relationship with bridge 15 between the first and second sides 18 and 19 and the first and second openings 24 and 25 such that the first hole 56 and the second hole 57, which reside at the distance 66 equal to the distance 32, align respectively with the first aperture 28 and the second aperture 29. The first fastener 41 via a threading therein inserts into the first hole 56 until the head 43 seats in the counterbore 58 and the shaft 45 extends through the lower segment 62 and into the first aperture 28 to a position whereby the shaft 45 resides at the lower surface 17 of the bridge 15 without protruding therefrom. Similarly, the second fastener 42 via a threading therein inserts into the second hole 57 until the head 44 seats in the counterbore 59 and the shaft 46 extends through the lower segment 63 and into the second aperture 29 to a position whereby the shaft 46 resides at the lower surface 17 of the bridge 15 without protruding therefrom. The engagement of the first fastener 41 with both the first hole 56 of the retention block 40 and the first aperture 28 of the bridge 15 and the second fastener 42 with both the second hole 57 of the retention block 40 and the second aperture 29 of the bridge 15 secures the retention block 40 with the bridge 15 across the transition section 22 whereby the retention block 40, which spans the transition section 22, mechanically constrains the bridge 15 and thus the implant 11 in order to hold the bridge 15 in the insertion form 34 and the implant 11 in the insertion shape 13 and prevent a transition of the bridge 15 from the insertion form 34 to the natural form 33 and the implant 11 from the insertion shape 13 to the natural shape 12.

In accordance with the orthopedic fixation system 10, the implant retainer 14, when loaded with the implant 11 in that the implant retainer 14 secures atop the bridge 15 as previously described, retains the implant 11 in its insertion shape 13 such that the implant 11 is ready for securing with bone, bones, or bone pieces, and, in particular, with a first bone and a second bone, which are presented herein as an example. The implant 11 in addition to its securing with and retention by the implant retainer 14 includes first and second drill guides secured respectively with the first and second openings 24 and 25 in order to facilitate a drilling of holes in the first and second bones.

A surgeon aligns the first bone with the second bone at a fusion zone in an orientation that promotes fixation of the first bone with the second bone and a proper healing thereof. The surgeon then places the implant 11 held in its insertion shape 13 by the implant retainer 14 across the first bone and the second bone with the transition section 22 of the bridge 15 located at the fusion zone. Upon placement of the implant 11, the surgeon secures the implant 11 with the first and second bones using first and second locating pin. The first locating pin inserts through the first drill guide and into the first bone thereby securing the implant 11 at its anchoring segment 26 with the first bone. Likewise, the second locating pin inserts through the second drill guide and into the second bone thereby securing the implant 11 at its anchoring segment 27 with the second bone. The first and second locating pins hold the implant 11 on the first and second bones with the first and second bones aligned in the orientation that promotes fixation. If desired, the surgeon may secure the first locating pin with the first drill guide via a first collar coupled with the first drill guide and the second locating pin with the second drill guide via a second collar coupled with the second drill guide.

After securing the implant 11 with the first and second bones, the surgeon creates drill holes in the first and second bones. The surgeon in a first procedure removes the first locating pin and the first collar if used, inserts a drill bit through the first drill guide and the first opening 24, and utilizes the drill bit to form a drill hole in the first bone at the first opening 24. Alternatively, the surgeon in a second procedure removes the first collar if used, inserts a cannulated drill bit over the first locating pin and through the first drill guide and the first opening 24, and utilizes the cannulated drill bit to form a drill hole in the first bone at the first opening 24.

With a drill hole formed in the first bone at the first opening 24, the surgeon removes the first drill guide from the first opening 24 and utilizes a depth gauge to determine the depth of the drill hole in the first bone. If the depth of the drill hole in the first bone is incorrect, the surgeon re-forms the drill hole in the first bone. When the depth of the drill hole in the first bone is correct, the surgeon confirms the alignment of the first and second bones remains in the orientation that promotes fixation, and then the surgeon inserts, via an insertion tool such as a screwdriver, an anchoring member in the form of a screw through the first opening 24 and into the first bone until the screw at a head thereof resides substantially, completely within the first opening 24, whereby the screw affixes the implant 11 at its anchoring segment 26 with the first bone.

Once the surgeon affixes the implant 11 at its anchoring segment 26 with the first bone, the surgeon affixes the implant 11 at its anchoring segment 27 with the second bone. In particular, the surgeon forms a drill hole in the second bone at the second opening 25 of the implant 11 employing either the first procedure or the second procedure, except the first or second procedure involves the second bone, the implant 11 at its second opening 25, the second drill guide, the second locating pin, and the second collar if used. The surgeon then measures the correctness of the drill hole in the second bone employing the previously described measuring procedure, except the measurement involves the second bone. Once the depth of the drill hole in the second bone is correct, the surgeon confirms the alignment of the first and second bones remains in the orientation that promotes fixation, and then, employing the previously described anchoring member insertion procedure to the second bone instead of the first bone, the surgeon inserts, via the insertion tool, an anchoring member in the form of a screw through the second opening 25 and into the second bone until the screw at a head thereof resides substantially, completely within the second opening 25, whereby, the screw affixes the implant 11 at its anchoring segment 27 with the second bone. While the foregoing shows forming a drill hole in the first bone and inserting an anchoring member therein followed by forming a drill hole in the second bone and inserting an anchoring member therein, one of ordinary skill in the art will recognize that the order of drill hole formation and anchoring member insertion may be reversed. Alternatively, one of ordinary skill in the art will recognize that, once a surgeon aligns the first bone with the second bone at the fusion zone and then places the implant 11 held in its insertion shape 13 by the implant retainer 14 across the first bone and the second bone with the transition section 22 of the bridge 15 located at the fusion zone, anchoring members in the form of self-tapping bone screws may be used to affix the implant 11 to the first bone and the second bone.

After affixing the implant 11 with the first and second bones across the fusion zone, the surgeon removes the first fastener 41 from the first aperture 28 of the implant 11 and if desired from the first hole 56 of the retention block 40 and the second fastener 42 from the second aperture 29 of the implant 11 and if desired from the second hole 57 of the retention block 40. With the fasteners 41 and 42 removed from engagement with the implant 11 and if desired from the retention block 40, the retention block 40 releases the implant 11, allowing the surgeon to remove the retention block 40 from atop the implant 11. The implant 11, which is completely released from the implant retainer 14, attempts transition from its insertion shape 13 to its natural shape 12 whereby the implant 11 delivers the energy stored in its transition section 22 to the first bone and the second bone, resulting in the implant 11 affixing the first bone and the second bone through an application of a compressive force to the fixation zone. The implant retainer 14 accordingly improves insertion of the implant 11 because the implant retainer 14 does not release its constraint of the implant 11 until the implant 11 is completely affixed to the first and second bones with its transition section 22 located across the fusion zone thereof such that the implant retainer 14 prevents the implant 11 from prematurely delivering the energy stored therein to the first and second bones at the fixation zone thereof.

Figure 5A:
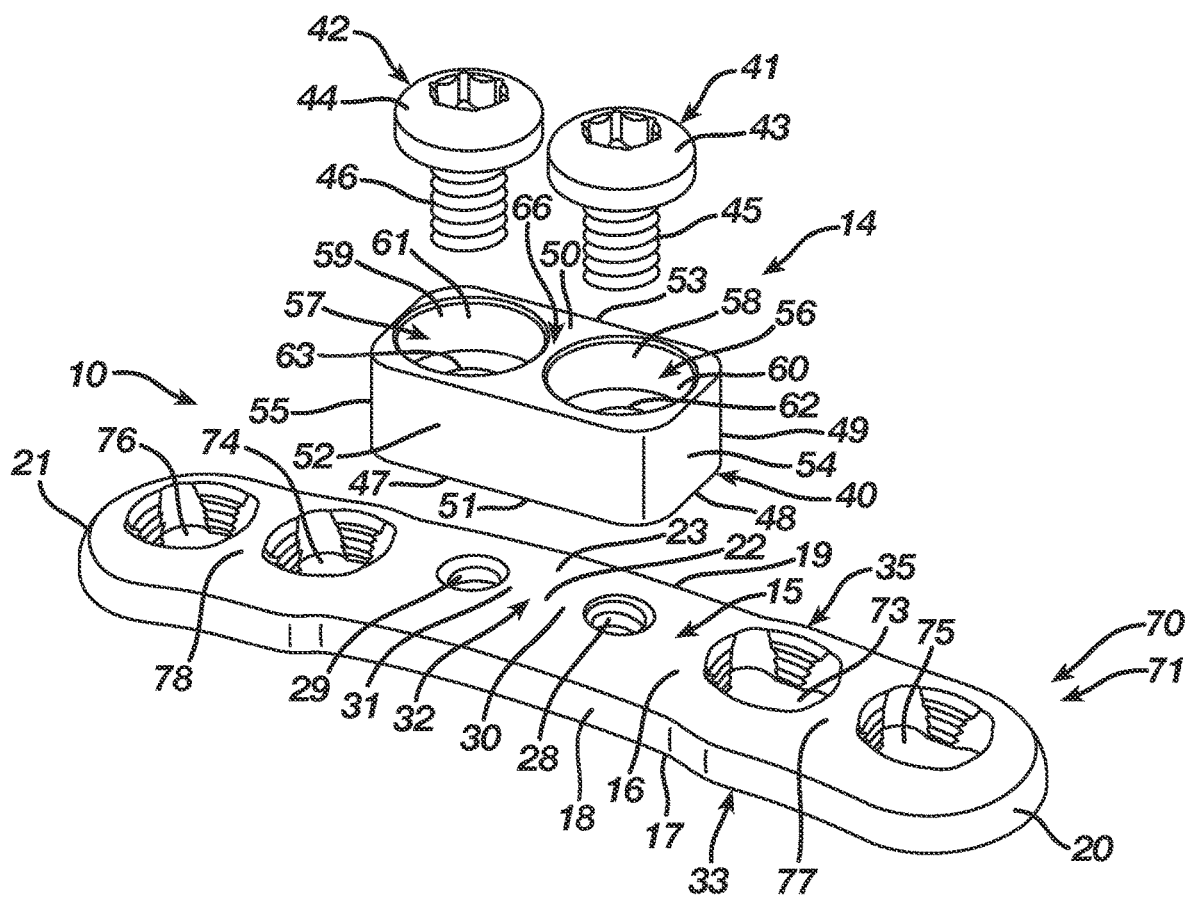
FIG. 5A is a top isometric view illustrating the orthopedic fixation system including the implant retainer disengaged from an orthopedic implant according to a second embodiment in a natural shape.
Figure 5B:
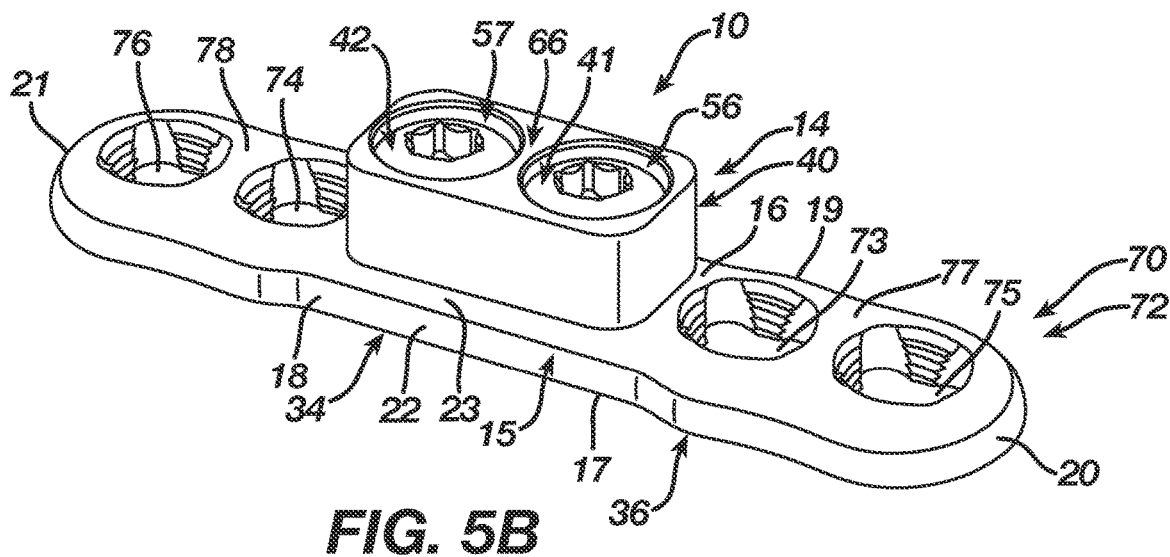
FIG. 5B is a top isometric view illustrating the orthopedic fixation system including the implant retainer engaged with the orthopedic implant according to the second embodiment in an insertion shape.
Figure 5C:
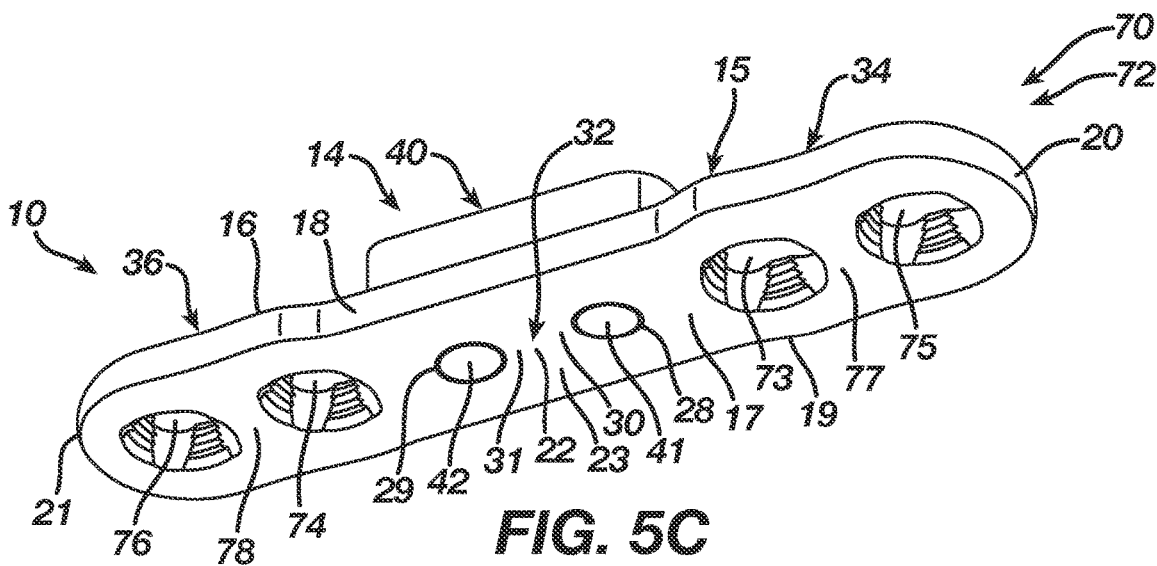
FIG. 5C is a bottom isometric view illustrating the orthopedic fixation system including the implant retainer engaged with the orthopedic implant according to the second embodiment in the insertion shape.
Figure 5D:
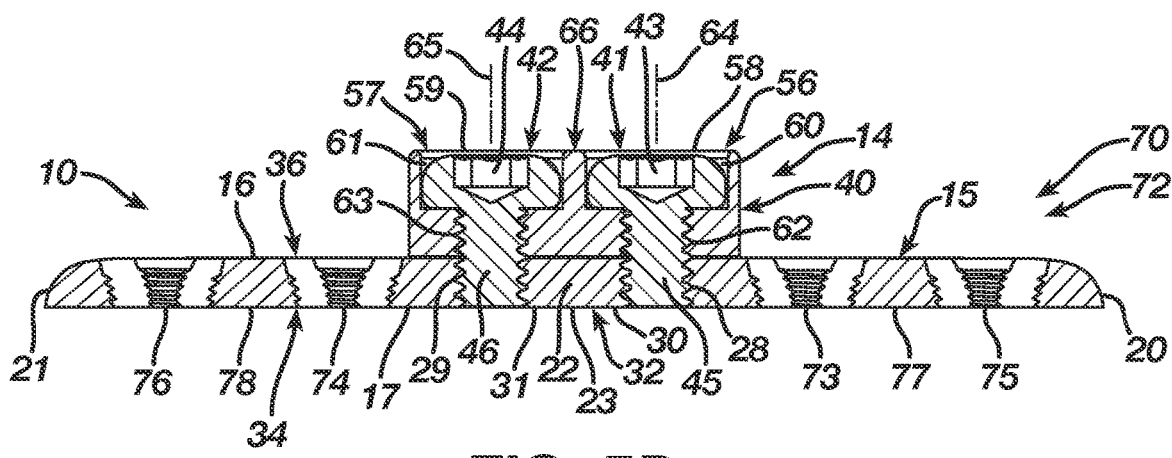
FIG. 5D is an elevation view in cross-section illustrating the orthopedic fixation system including the implant retainer engaged with the orthopedic implant according to the second embodiment in the insertion shape.

The orthopedic fixation system 10 as illustrated in FIGS. 5E-5D includes the implant retainer 14 and an orthopedic implant 70 according to a second embodiment transitionable between a natural shape 71 and an insertion shape 72. The implant 70 is substantially similar in design and operation relative to the implant 11 according to the first embodiment such that, for the sake of brevity, only differences therebetween will be described herein. Moreover, one of ordinary skill in the art will recognize that like parts of the implant 70 labeled with like numerals of the implant 11 incorporate a design and function as previously set forth in the detailed description of the implant 11 according to the first embodiment. The implant 11 includes the first opening 24 at the anchoring segment 26 and the second opening 25 at the anchoring segment 27, whereas the implant 70 includes first and third openings 73 and 75 at an anchoring segment 77 and second and fourth openings 74 and 76 at an anchoring segment 78 that receive additional drill guides or anchoring members in the form of screws therethrough in order to more securely affix the implant 70 to bone, bones, or bone pieces. The implant retainer 14 engages the implant 70 according to the second embodiment and constrains the implant 70 in the insertion shape 72 substantially, completely identical to the implant 11 according to the first embodiment. Securing the implant 70 to bone, bones, or bone pieces for affixation thereof is substantially similar to the implant 11 as previously described, except the implant 70, during insertion of screws into the bone, bones, or bone pieces using the first and second openings 73 and 74, remains secured with the bone, bones, or bone pieces via locating pins inserted through the third and fourth openings 75 and 76, and the implant 70 secures with the bone, bones, or bone pieces using screws inserted through the third and fourth openings 75 and 76. The implant retainer 14 releases the implant 70 according to the second embodiment for attempted transition from the insertion shape 72 to the natural shape 71 substantially, completely identical to the implant 11 according to the first embodiment.

The orthopedic fixation system 10 as illustrated in FIGS. 6A-6D includes an orthopedic implant 80 according to a fourth embodiment transitionable between a natural shape 81 and an insertion shape 82. The implant 80 is substantially similar in design and operation relative to the implant 11 according to the first embodiment, except the implant 80 includes a Y-shaped configuration that facilitates affixation of the implant 80 with different sized and shaped bone, bones, or bone pieces. The orthopedic fixation system 10 further includes the implant retainer 14 configured to engage the implant 80 and constrain the implant 80 in the insertion shape 82.

Figure 6A:
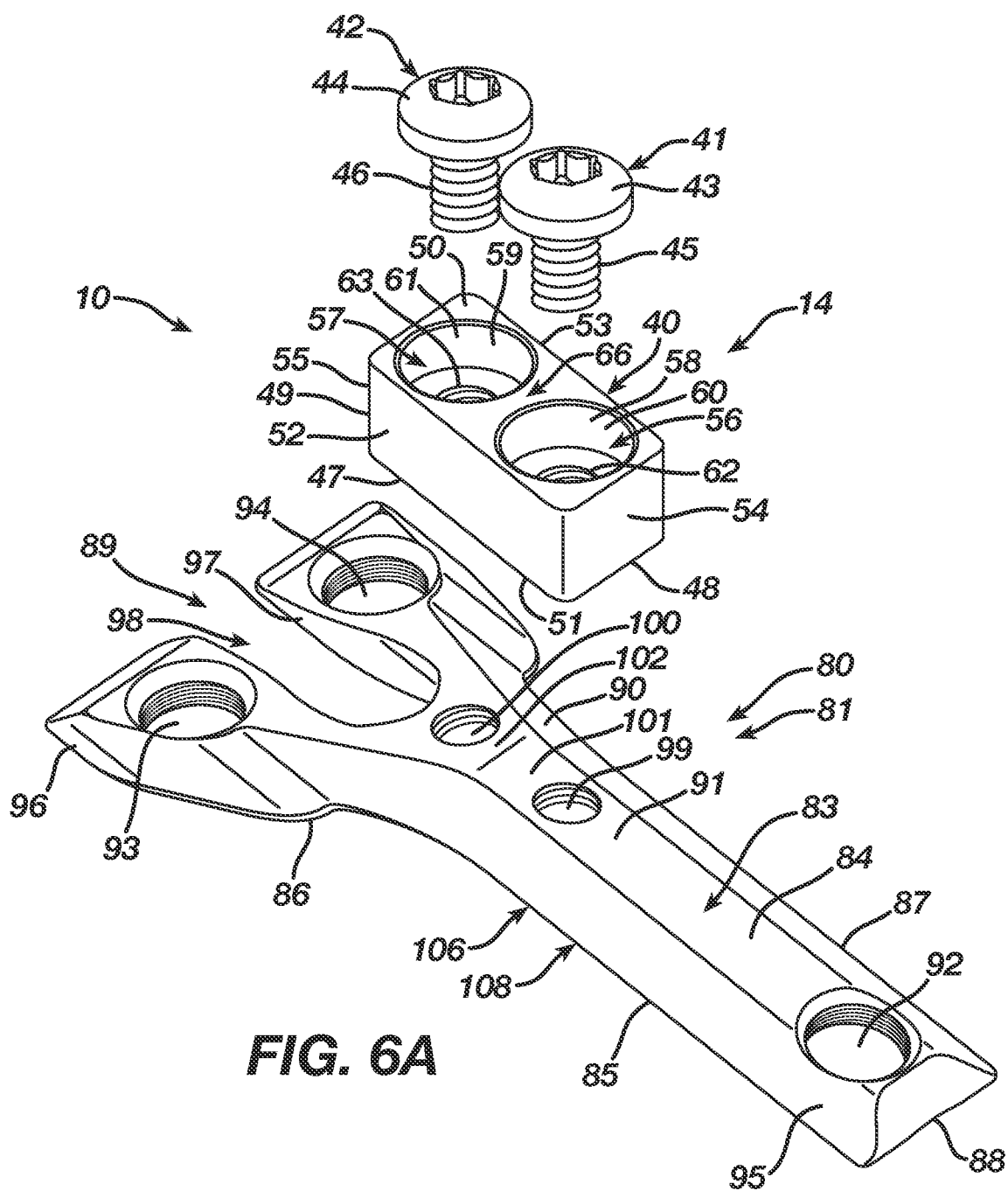
FIG. 6A is a top isometric view illustrating the orthopedic fixation system including the implant retainer disengaged from an orthopedic implant according to a fourth embodiment in a natural shape.
Figure 6B:
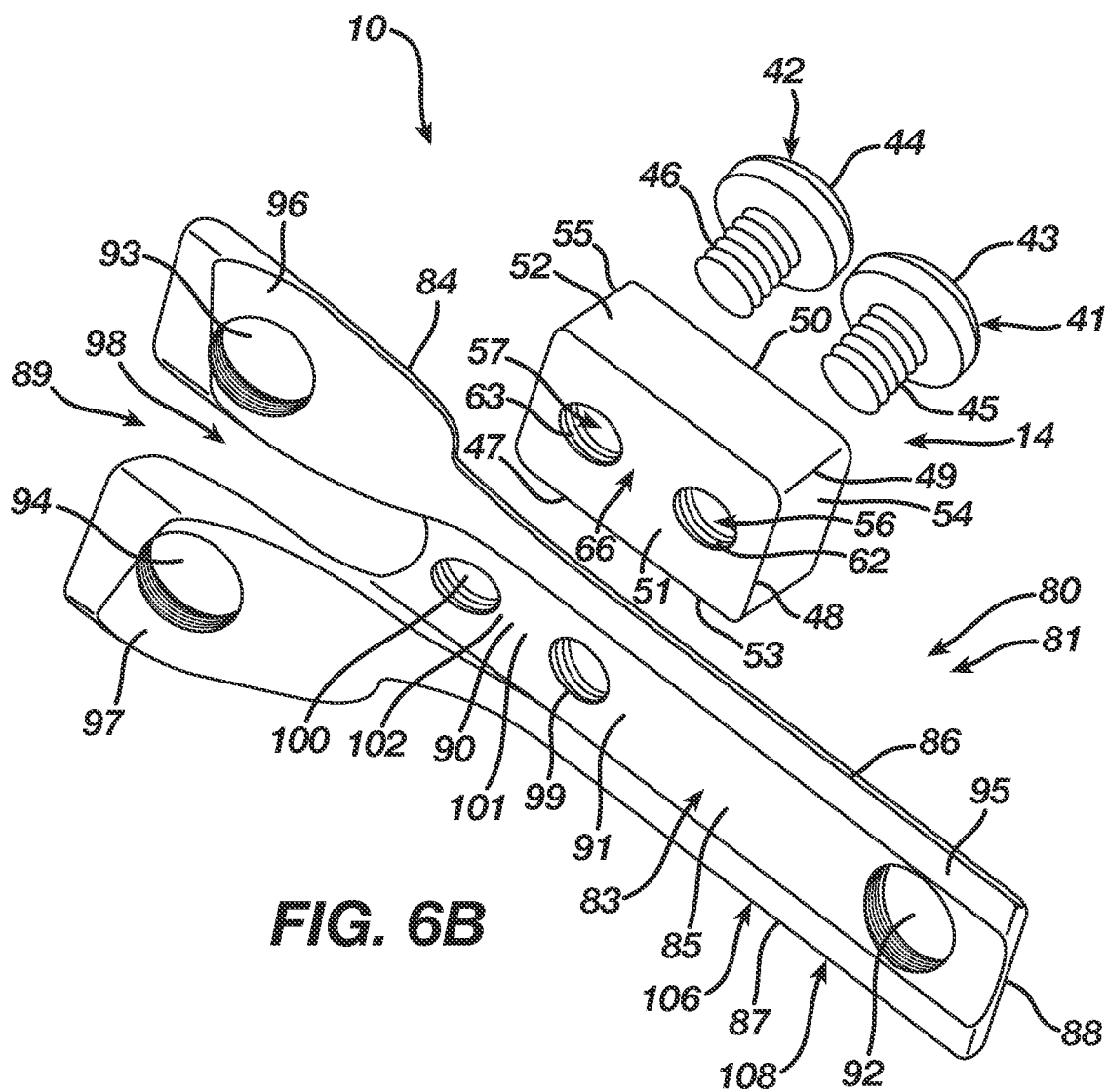
FIG. 6B is a bottom isometric view illustrating the orthopedic fixation system including the implant retainer disengaged from the orthopedic implant according to the fourth embodiment in the natural shape.
Figure 6C:
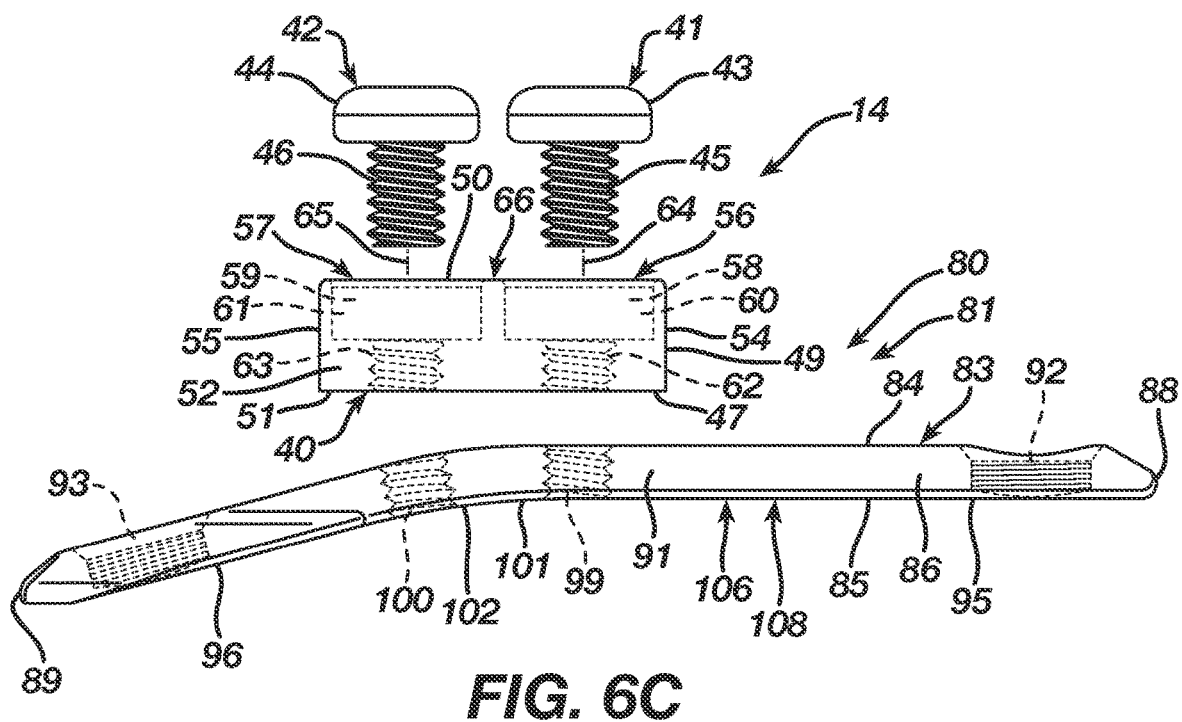
FIG. 6C is an elevation view illustrating the orthopedic fixation system including the implant retainer disengaged from the orthopedic implant according to the fourth embodiment in the natural shape.
Figure 6D:
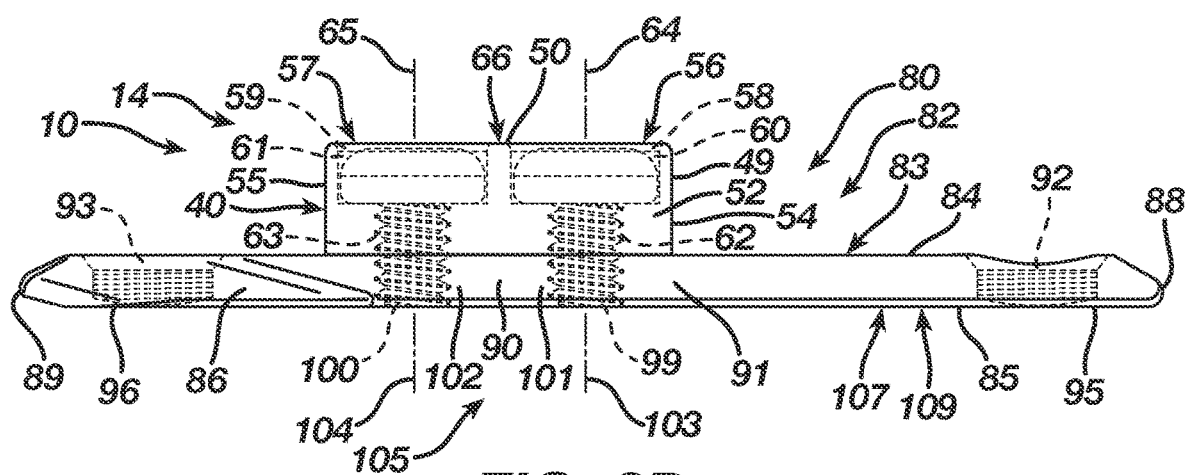
FIG. 6D is an elevation view illustrating the orthopedic fixation system including the implant retainer engaged with the orthopedic implant according to the fourth embodiment in an insertion shape.

FIGS. 6A-6C illustrate the orthopedic implant 80 according to the fourth embodiment in the natural shape 81, whereas FIG. 6D illustrates the orthopedic implant 80 in the insertion shape 82. The implant 80 in the fourth embodiment may be manufactured from a shape memory material with superelastic or temperature dependent properties (e.g., Nitinol) such that the implant 80 transitions between the natural shape 81 and the insertion shape 82. The implant 80 when deformed from the natural shape 81 to the insertion shape 82 stores energy deliverable to bone, bones, or bone pieces. In accordance with its manufacture from shape memory material, the implant 80 begins in the natural shape 81, is transitionable to the insertion shape 82, and, once implanted in bone, bones, or bone pieces, attempts to transition from the insertion shape 82 to the natural shape 81 whereby the implant 80 delivers the energy stored therein in order to affix the bone, bones, or bone pieces and promote a healing thereof. In the fourth embodiment, attempted transition of the implant 80 from the insertion shape 82 to the natural shape 81 continuously compresses the bone, bones, or bone pieces to promote fusion thereof.

The implant 80 includes a bridge 83 with upper and lower surfaces 84 and 85, first and second sides 86 and 87, and first and second ends 88 and 89. The implant 80 includes a transition section 90 located adjacent a center section 91 of the implant 80 and thus the bridge 83 between the center section 91 and the second end 89. The implant 80, and thus the bridge 83, includes a first opening 92 extending therethrough from the upper surface 84 to the lower surface 85 whereby the first opening 92 is located adjacent the first end 88 of the bridge 83 to provide the implant 80 and thus the bridge 83 with a first anchoring segment 95. The implant 80, and thus the bridge 83, includes second and third openings 93 and 94 extending therethrough from the upper surface 84 to the lower surface 85 whereby the second and third openings 93 and 94 are aligned and located adjacent the second end 89 of the bridge 83. In the fourth embodiment, the implant 80, and thus the bridge 83, at the second end 89 divides via a cut-out 98 into a second anchoring segment 96 incorporating the second opening 93 and a third anchoring segment 97 incorporating the third opening 94, thereby producing a Y-shaped configuration for the implant 80. The first, second, and third openings 92-94 receive anchoring members in the form of screws therethrough in order to facilitate a securing of the implant 80 at the first, second, and third anchoring segments 95-97 with bone, bones, or bone pieces whereby the bridge 83 between the first opening 92 and the second and third openings 93-94 traverses a fixation zone of the bone, bones, or bone pieces such that the implant 80, after its affixation and attempted transition from the insertion shape 82 to the natural shape 81, delivers energy to the bone, bones, or bone pieces at the fixation zone. Although the first, second, and third openings 92-94 of the implant 80 primarily operate to receive therethrough anchoring members, the first, second, and third openings 92-94 may receive therein respectively drill guides. The drill guides facilitate a drilling of holes in the bone, bones, or bone pieces that assist in inserting anchoring members through the first, second, and third openings 92-94 and into the bone, bones, or bone pieces. The first, second, and third openings 92-94 in the fourth embodiment include threads that facilitate engagement of the first, second, and third openings 92-94 with anchoring members or the drill guides. While the implant 80 in the fourth embodiment includes the first, second, and third openings 92-94 in the first, second, and third anchoring segments 95-97, one of ordinary skill in the art will recognize that the implant 80 may include additional openings in the first, second, and third anchoring segments 95-97 that receive additional anchoring members in the form of screws therethrough in order to more securely affix the implant 80 to bone, bones, or bone pieces.

The implant 80, and thus the bridge 83, includes a first securing feature in the form of a first aperture 99, which is preferably threaded, extending therethrough from the upper surface 84 to the lower surface 85. The first aperture 99 preferably is located adjacent the transition section 90 at a first side 101 thereof. Similarly, the implant 80, and thus the bridge 83, includes a second securing feature in the form a second aperture 100, which is preferably threaded, extending therethrough from the upper surface 84 to the lower surface 85. The second aperture 100 preferably is located adjacent the transition section 90 at a second side 102 thereof. The first aperture 99 and the second aperture 100 provide engagement points for the implant retainer 14 with the implant 80. As such, the first aperture 99 at a vertical axis 103 and the second aperture 100 at a vertical axis 104, when the implant 80 resides in the insertion shape 82, are spaced apart across the transition section 90 a distance 105 that allows the first and second apertures 99 and 100 to facilitate a securing of the implant retainer 14 with the implant 80 at the transition section 90.

The regular inherent shape of the implant 80, as illustrated in FIGS. 6A-6C, is its natural shape 81 where the transition section 90 locates the bridge 83 in a natural form 106 consisting of a closed or angular profile whereby the first and second ends 88 and 89 reside at a first distance 108. Nevertheless, as illustrated in FIGS. 8D, the implant 80 is deformable under the action of superelasticity or temperature dependent shape memory to its insertion shape 82 where the transition section 90 deforms to store energy while also moving the bridge 83 from its natural form 106 to an insertion form 107 which is an open or substantially linear profile whereby the first and second ends 88 and 89 reside at a second distance 109 that is greater than the first distance 108. Since the insertion shape 82 is not the regular inherent shape of the implant 80, the bridge 83 typically is mechanically constrained using the implant retainer 14 whereby the implant retainer 14 maintains the bridge 83 in its insertion form 107. In particular, the implant retainer 14 couples with the implant 80 via the first and second apertures 99 and 100, which are located at the distance 105 due to the implant 80 residing in the insertion shape 82, such that the implant retainer 14 holds the bridge 83 in the insertion form 107, resulting in the implant retainer 14 constraining the deformed transition section 90 in order to maintain the implant 80 in its insertion shape 82. After implantation into bone, bones, or bone pieces and a release of the implant retainer 14, including, if necessary, a heating of the implant 80, the implant 80 delivers the energy stored in the transition section 90 whereby the bridge 83 attempts to transition from its insertion form 107 to its natural form 106 such that the implant 80, which attempts transition from its insertion shape 82 to its natural shape 81, affixes the bone, bones, or bone pieces through an application of a compressive force thereto.

During formation of the orthopedic fixation system 10 through a securing of the implant retainer 14 with the implant 80 as illustrated in FIGS. 6A-6D, the implant 80 is mechanically deformed from the natural shape 81 to the insertion shape 82 such that the implant 80 stores mechanical energy. Mechanical deformation of the implant 80 may include cooling of the implant 80 whereby the implant 80 transitions from its austenite phase to its martensite phase in order to facilitate an easier mechanical deformation of the implant 80 from its natural shape 81 to its insertion shape 82 prior to a loading of the implant retainer 14 with the implant 80. Upon mechanical deformation of the implant 80 whereby the transition section 90 deforms to store energy while also moving the bridge 83 from its natural form 106 where the first and second ends 88 and 89 reside at the first distance 108 to its insertion form 107 where the first and second ends 88 and 89 reside at the second distance 109, the first aperture 99 and the second aperture 100 due to the movement of the bridge 83 now are spaced apart across the transition section 90 the distance 105. With the bridge 83 in its insertion form 106 and the first and second apertures 99 and 100 residing at the distance 105, the retention block 40 seats atop the bridge 83 at the upper surface 84 thereof in abutting relationship with bridge 83 between the first and second sides 86 and 87 and the first opening 92 and the second and third openings 93 and 94 such that the first hole 56 and the second hole 57, which reside at the distance 66 equal to the distance 105, align respectively with the first aperture 99 and the second aperture 100. The first fastener 41 via a threading therein inserts into the first hole 56 until the head 43 seats in the counterbore 58 and the shaft 45 extends through the lower segment 62 and into the first aperture 99 to a position whereby the shaft 45 resides at the lower surface 85 of the bridge 83 without protruding therefrom. Similarly, the second fastener 42 via a threading therein inserts into the second hole 57 until the head 44 seats in the counterbore 59 and the shaft 46 extends through the lower segment 63 and into the second aperture 100 to a position whereby the shaft 46 resides at the lower surface 85 of the bridge 83 without protruding therefrom. The engagement of the first fastener 41 with both the first hole 56 of the retention block 40 and the first aperture 99 of the bridge 83 and the second fastener 42 with both the second hole 57 of the retention block 40 and the second aperture 100 of the bridge 83 secures the retention block 40 with the bridge 83 across the transition section 90 whereby the retention block 40, which spans the transition section 90, mechanically constrains the bridge 83 and thus the implant 80 in order to hold the bridge 83 in the insertion form 107 and the implant 80 in the insertion shape 82 and prevent a transition of the bridge 83 from the insertion form 107 to the natural form 106 and the implant 80 from the insertion shape 82 to the natural shape 81.

In accordance with the orthopedic fixation system 10, the implant retainer 14, when loaded with the implant 80 in that the implant retainer 14 secures atop the bridge 83 as previously described, retains the implant 80 in its insertion shape 82 such that the implant 80 is ready for securing with bone, bones, or bone pieces. The implant 80 in addition to its securing with and retention by the implant retainer 14 includes first, second, and third drill guides secured respectively with the first, second, and third openings 92-94 in order to facilitate a drilling of holes in the bone, bones, or bone pieces. Securing the implant 80 to bone, bones, or bone pieces for affixation thereof is substantially similar to the implant 11 as previously described, except, during affixation of the implant 80 with the bone, bones, or bone pieces, the implant 80 secures with the bone, bones, or bone pieces using screws inserted through the first, second, and third openings 92-94. Removal of the implant retainer 14 from atop the bridge 83 of the implant 80 involves removing the first fastener 41 from the first aperture 99 of the bridge 83 and if desired from the first hole 56 of the retention block 40 and the second fastener 42 from the second aperture 100 of the bridge 83 and if desired from the second hole 57 of the retention block 40 prior to the withdrawal of the retention block 40 from atop the implant 80. The implant 80, which is completely released from the implant retainer 14, attempts transition from its insertion shape 82 to its natural shape 81 whereby the implant 80 delivers the energy stored in its transition section 90 to the bone, bones, or bone pieces, resulting in the implant 80 affixing the bone, bones, or bone pieces through an application of a compressive force thereto at a fixation zone.

The orthopedic fixation system 10 as illustrated in FIGS. 7A-7D includes an orthopedic implant 110 according to a fifth embodiment transitionable between a natural shape 111 and an insertion shape 112. The implant 110 is substantially similar in design and operation relative to the implant 11 according to the first embodiment, except the implant 80 includes an H-shaped configuration that facilitates affixation of the implant 110 with different sized and shaped bone, bones, or bone pieces. The orthopedic fixation system 10 further includes the implant retainer 14 configured to engage the implant 110 and constrain the implant 110 in the insertion shape 112.

Figure 7A:
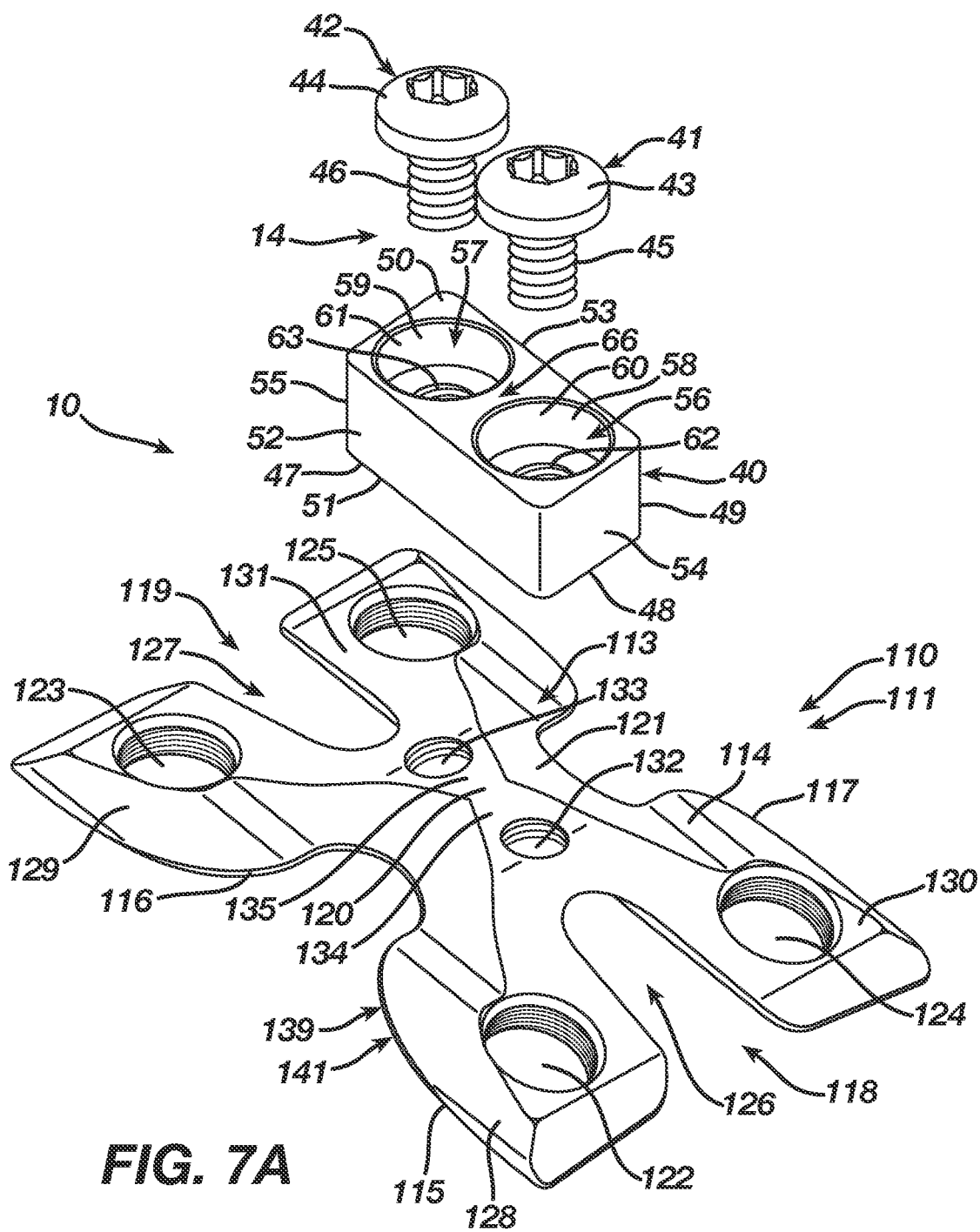
FIG. 7A is a top isometric view illustrating the orthopedic fixation system including the implant retainer disengaged from an orthopedic implant according to a fifth embodiment in a natural shape.
Figure 7B:
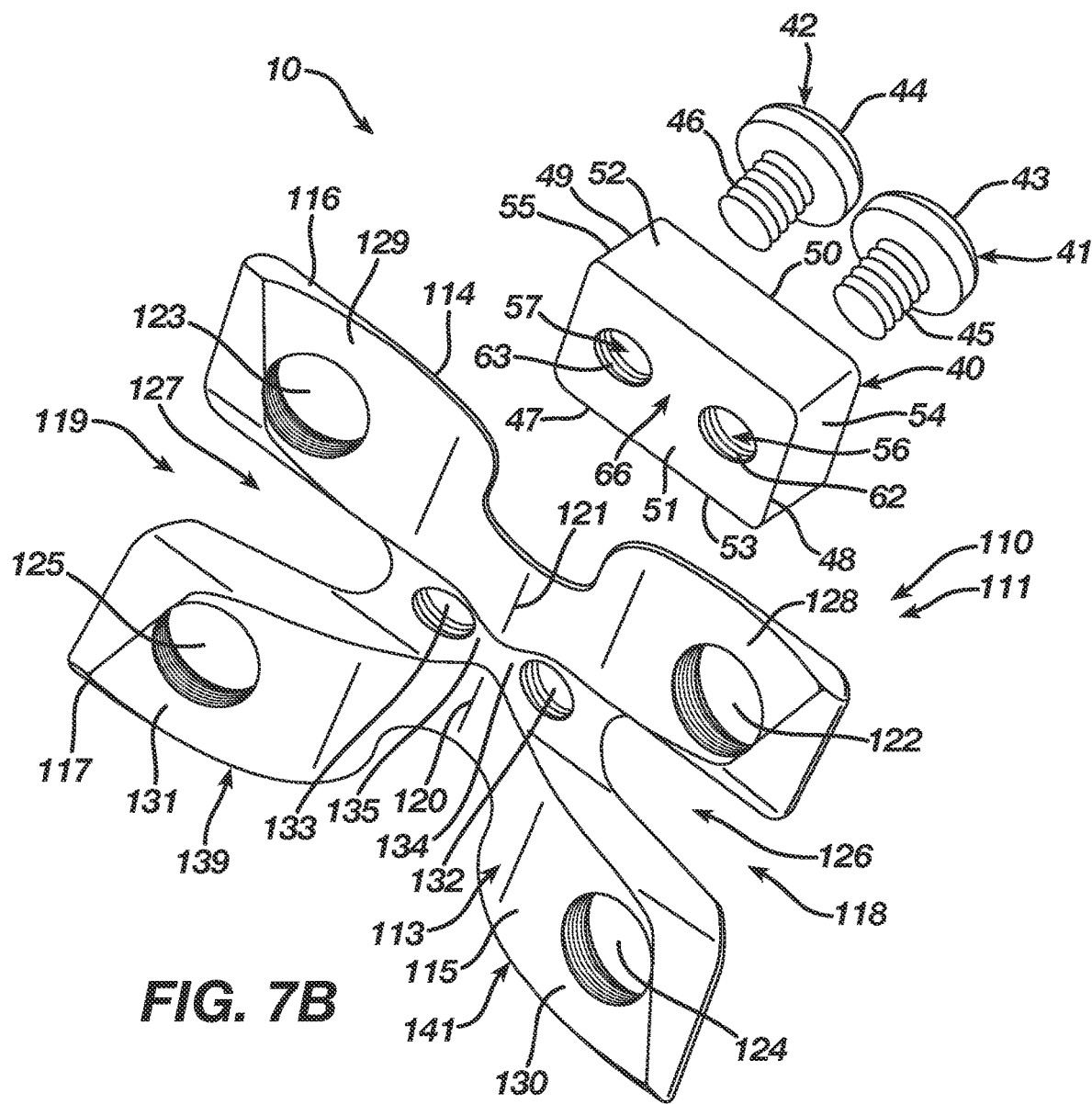
FIG. 7B is a bottom isometric view illustrating the orthopedic fixation system including the implant retainer disengaged from the orthopedic implant according to the fifth embodiment in the natural shape.
Figure 7C:
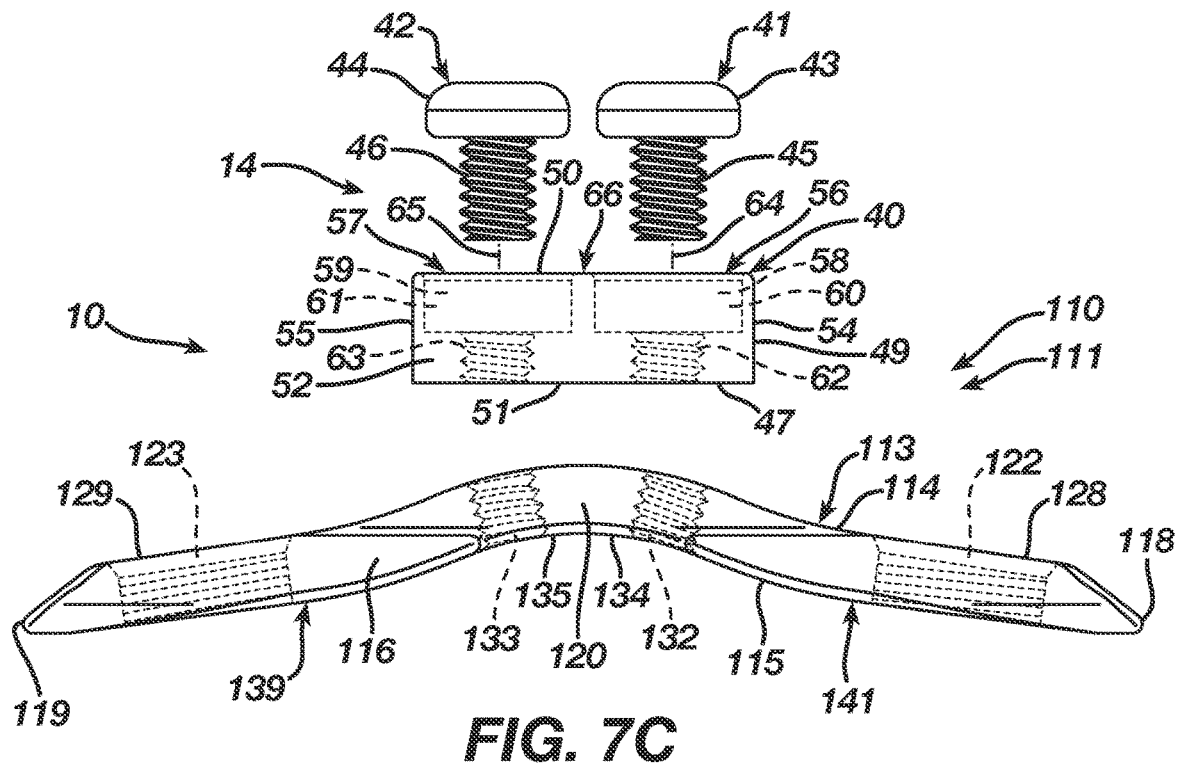
FIG. 7C is an elevation view illustrating the orthopedic fixation system including the implant retainer disengaged from the orthopedic implant according to the fifth embodiment in the natural shape.
Figure 7D:
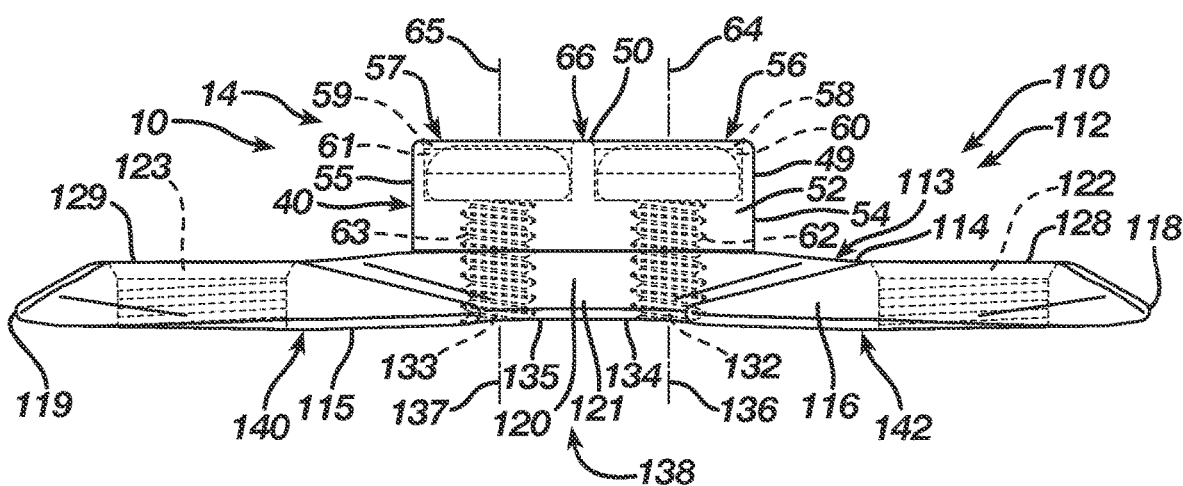
FIG. 7D is an elevation view illustrating the orthopedic fixation system including the implant retainer engaged with the orthopedic implant according to the fifth embodiment in an insertion shape.

FIGS. 7A-7C illustrate the orthopedic implant 110 according to the fifth embodiment in the natural shape 111, whereas FIG. 7D illustrates the orthopedic implant 110 in the insertion shape 112. The implant 110 in the fifth embodiment may be manufactured from a shape memory material with superelastic or temperature dependent properties (e.g., Nitinol) such that the implant 110 transitions between the natural shape 111 and the insertion shape 112. The implant 110 when deformed from the natural shape 111 to the insertion shape 112 stores energy deliverable to bone, bones, or bone pieces. In accordance with its manufacture from shape memory material, the implant 110 begins in the natural shape 111, is transitionable to the insertion shape 112, and, once implanted in bone, bones, or bone pieces, attempts to transition from the insertion shape 112 to the natural shape 111 whereby the implant 110 delivers the energy stored therein to the bone, bones, or bone pieces in order to affix the bone, bones, or bone pieces and promote a healing thereof. In the fifth embodiment, attempted transition of the implant 110 from the insertion shape 112 to the natural shape 111 continuously compresses the bone, bones, or bone pieces to promote fusion thereof.

The implant 110 includes a bridge 113 with upper and lower surfaces 114 and 115, first and second sides 116 and 117, and first and second ends 118 and 119. The implant 110 includes a transition section 120 located at a center section 121 of the implant 110 and thus the bridge 113. The implant 110, and thus the bridge 113, includes first and third openings 122 and 124 extending therethrough from the upper surface 114 to the lower surface 115 whereby the first and third openings 122 and 124 are aligned and located adjacent the first end 118 of the bridge 113. The implant 110, and thus the bridge 113, includes second and fourth openings 123 and 125 extending therethrough from the upper surface 114 to the lower surface 115 whereby the second and fourth openings 123 and 125 are aligned and located adjacent the second end 119 of the bridge 113. In the fifth embodiment, the implant 110, and thus the bridge 113, at the first end 118 divides via a cut-out 126 into a first anchoring segment 128 incorporating the first opening 122 and a third anchoring segment 130 incorporating the third opening 124 and at the second end 119 divides via a cut-out 127 into a second anchoring segment 129 incorporating the second opening 123 and a fourth anchoring segment 131 incorporating the fourth opening 125, thereby producing an H-shaped configuration for the implant 110. The first, second, third, and fourth openings 122-125 receive anchoring members in the form of screws therethrough in order to facilitate a securing of the implant 110 at the first, second, third and fourth anchoring segments 128-131 with bone, bones, or bone pieces whereby the bridge 113 between the first and second openings 122 and 124 and the second and fourth openings 123 and 125 traverses a fixation zone of the bone, bones, or bone pieces such that the implant 110, after its affixation and attempted transition from the insertion shape 122 to the natural shape 121, delivers energy to the bone, bones, or bone pieces at the fixation zone. Although the first, second, third, and fourth openings 122-125 of the implant 110 primarily operate to receive therethrough anchoring members, the first, second, third, and fourth openings 122-125 may receive therein respectively drill guides. The drill guides facilitate a drilling of holes in the bone, bones, or bone pieces that assist in inserting anchoring members through the first, second, third, and fourth openings 122-125 and into the bone, bones, or bone pieces. The first, second, third, and fourth openings 122-125 in the fifth embodiment include threads that facilitate engagement of the first, second, third, and fourth openings 122-125 with anchoring members or the drill guides. While the implant 110 in the fifth embodiment includes the first, second, third, and fourth openings 122-125 in the first, second, third and fourth anchoring segments 128-131, one of ordinary skill in the art will recognize that the implant 110 may include additional openings in the first, second, third and fourth anchoring segments 128-131 that receive additional anchoring members in the form of screws therethrough in order to more securely affix the implant 110 to bone, bones, or bone pieces.

The implant 110, and thus the bridge 113, includes a first securing feature in the form of a first aperture 132, which is preferably threaded, extending therethrough from the upper surface 114 to the lower surface 115. The first aperture 132 preferably is located adjacent the transition section 120 at a first side 134 thereof. Similarly, the implant 110, and thus the bridge 113, includes a second securing feature in the form a second aperture 133, which is preferably threaded, extending therethrough from the upper surface 114 to the lower surface 115. The second aperture 133 preferably is located adjacent the transition section 120 at a second side 135 thereof. The first aperture 132 and the second aperture 133 provide engagement points for the implant retainer 14 with the implant 110. As such, the first aperture 132 at a vertical axis 136 and the second aperture 133 at a vertical axis 137, when the implant 110 resides in the insertion shape 112, are spaced apart across the transition section 120 a distance 138 that allows the first and second apertures 132 and 133 to facilitate a securing of the implant retainer 14 with the implant 110 at the transition section 120.

The regular inherent shape of the implant 110, as illustrated in FIGS. 7A-7C, is its natural shape 111 where the transition section 120 locates the bridge 113 in a natural form 139 consisting of a closed or angular profile whereby the first and second ends 118 and 119 reside at a first distance 141. Nevertheless, as illustrated in FIG. 7D, the implant 110 is deformable under the action of superelasticity or temperature dependent shape memory to its insertion shape 112 where the transition section 120 deforms to store energy while also moving the bridge 113 from its natural form 139 to an insertion form 140 which is an open or substantially linear profile whereby the first and second ends 118 and 119 reside at a second distance 142 that is greater than the first distance 141. Since the insertion shape 112 is not the regular inherent shape of the implant 110, the bridge 113 typically is mechanically constrained using the implant retainer 14 whereby the implant retainer 14 maintains the bridge 113 in its insertion form 140. In particular, the implant retainer 14 couples with the implant 110 via the first and second apertures 132 and 133, which are located at the distance 138 due to the implant 110 residing in the insertion shape 112, such that the implant retainer 14 holds the bridge 113 in the insertion form 140, resulting in the implant retainer 14 constraining the deformed transition section 120 in order to maintain the implant 110 in its insertion shape 112. After implantation into bone, bones, or bone pieces and a release of the implant retainer 14, including, if necessary, a heating of the implant 110, the implant 110 delivers the energy stored in the transition section 120 whereby the bridge 113 attempts to transition from its insertion form 140 to its natural form 139 such that the implant 110, which attempts transition from its insertion shape 112 to its natural shape 111, affixes the bone, bones, or bone pieces through an application of a compressive force thereto.

During formation of the orthopedic fixation system 10 through a securing of the implant retainer 14 with the implant 110 as illustrated in FIGS. 7A-7D, the implant 110 is mechanically deformed from the natural shape 111 to the insertion shape 112 such that the implant 110 stores mechanical energy. Mechanical deformation of the implant 110 may include cooling of the implant 110 whereby the implant 110 transitions from its austenite phase to its martensite phase in order to facilitate an easier mechanical deformation of the implant 110 from its natural shape 111 to its insertion shape 112 prior to a loading of the implant retainer 14 with the implant 110. Upon mechanical deformation of the implant 110 whereby the transition section 120 deforms to store energy while also moving the bridge 113 from its natural form 139 where the first and second ends 118 and 119 reside at the first distance 141 to its insertion form 140 where the first and second ends 118 and 119 reside at the second distance 142, the first aperture 132 and the second aperture 133 due to the movement of the bridge 113 now are spaced apart across the transition section 120 the distance 138. With the bridge 113 in its insertion form 140 and the first and second apertures 132 and 133 residing at the distance 138, the retention block 40 seats atop the bridge 113 at the upper surface 114 thereof in abutting relationship with bridge 113 between the first and second sides 116 and 117 and the first and third openings 122 and 124 and the second and fourth openings 123 and 125 such that the first hole 56 and the second hole 57, which reside at the distance 66 equal to the distance 138, align respectively with the first aperture 132 and the second aperture 133. The first fastener 41 via a threading therein inserts into the first hole 56 until the head 43 seats in the counterbore 58 and the shaft 45 extends through the lower segment 62 and into the first aperture 132 to a position whereby the shaft 45 resides at the lower surface 115 of the bridge 113 without protruding therefrom. Similarly, the second fastener 42 via a threading therein inserts into the second hole 57 until the head 44 seats in the counterbore 59 and the shaft 46 extends through the lower segment 63 and into the second aperture 133 to a position whereby the shaft 46 resides at the lower surface 115 of the bridge 113 without protruding therefrom. The engagement of the first fastener 41 with both the first hole 56 of the retention block 40 and the first aperture 132 of the bridge 113 and the second fastener 42 with both the second hole 57 of the retention block 40 and the second aperture 133 of the bridge 113 secures the retention block 40 with the bridge 113 across the transition section 120 whereby the retention block 40, which spans the transition section 120, mechanically constrains the bridge 113 and thus the implant 110 in order to hold the bridge 113 in the insertion form 140 and the implant 110 in the insertion shape 112 and prevent a transition of the bridge 113 from the insertion form 140 to the natural form 139 and the implant 110 from the insertion shape 112 to the natural shape 111.

In accordance with the orthopedic fixation system 10, the implant retainer 14, when loaded with the implant 110 in that the implant retainer 14 secures atop the bridge 113 as previously described, retains the implant 110 in its insertion shape 112 such that the implant 110 is ready for securing with bone, bones, or bone pieces. The implant 110 in addition to its securing with and retention by the implant retainer 14 includes first, second, third, and fourth drill guides secured respectively with the first, second, third, and fourth openings 122-125 in order to facilitate a drilling of holes in the bone, bones, or bone pieces. Securing the implant 110 to bone, bones, or bone pieces for affixation thereof is substantially similar to the implant 11 as previously described, except, during affixation of the implant 80 with the bone, bones, or bone pieces, the implant 80 secures with the bone, bones, or bone pieces using screws inserted through the first, second, third, and fourth openings 122-125. Removal of the implant retainer 14 from atop the bridge 113 of the implant 110 involves removing the first fastener 41 from the first aperture 132 of the bridge 113 and if desired from the first hole 56 of the retention block 40 and the second fastener 42 from the second aperture 133 of the bridge 113 and if desired from the second hole 57 of the retention block 40 prior to the withdrawal of the retention block 40 from atop the implant 110. The implant 110, which is completely released from the implant retainer 14, attempts transition from its insertion shape 112 to its natural shape 111 whereby the implant 110 delivers the energy stored in its transition section 120 to the bone, bones, or bone pieces, resulting in the implant 110 affixing the bone, bones, or bone pieces through an application of a compressive force thereto at a fixation zone.

The orthopedic fixation system 10 as illustrated in FIGS. 8A-8D includes an orthopedic implant 150 according to a sixth embodiment transitionable between a natural shape 151 and an insertion shape 152. The implant 150 is similar in design and operation relative to the implant 11 according to the first embodiment, except the implant 150 includes integrated anchoring members that facilitate affixation of the implant 150 with bone, bones, or bone pieces. The orthopedic fixation system 10 further includes the implant retainer 14 configured to engage the implant 150 and constrain the implant 150 in the insertion shape 152.

Figure 8A:
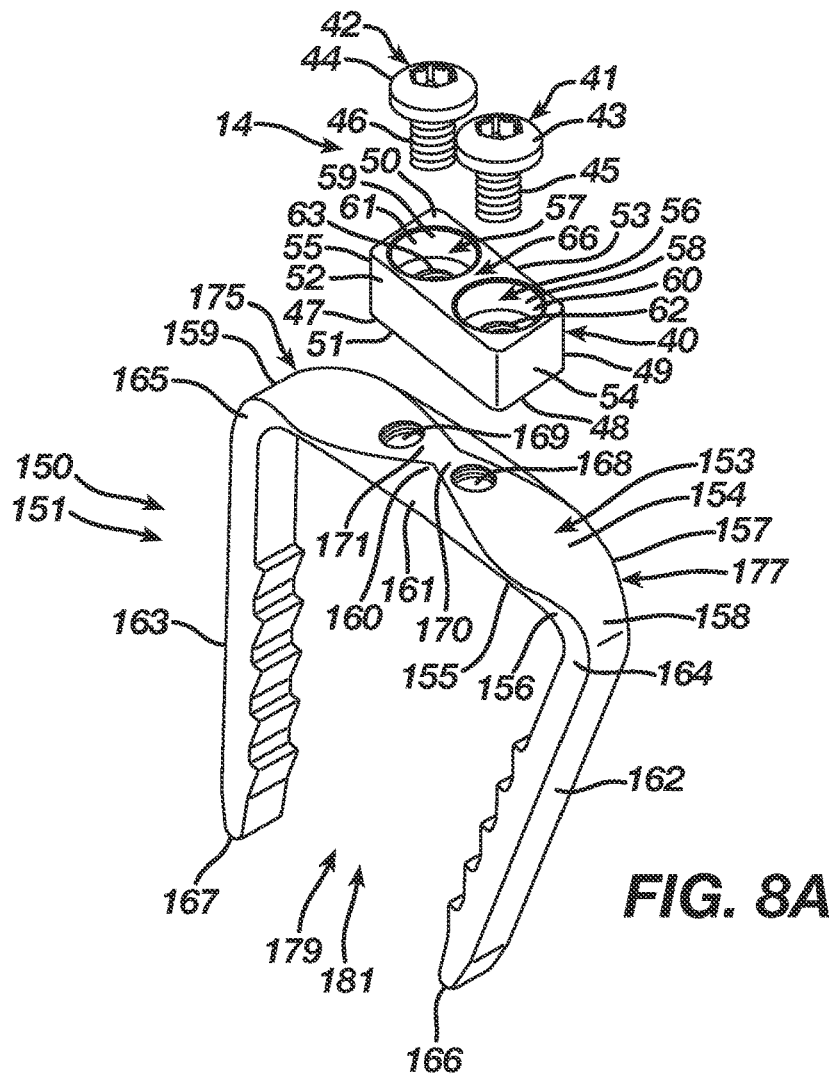
FIG. 8A is a top isometric view illustrating the orthopedic fixation system including the implant retainer disengaged from an orthopedic implant according to a sixth embodiment in a natural shape.
Figure 8B:
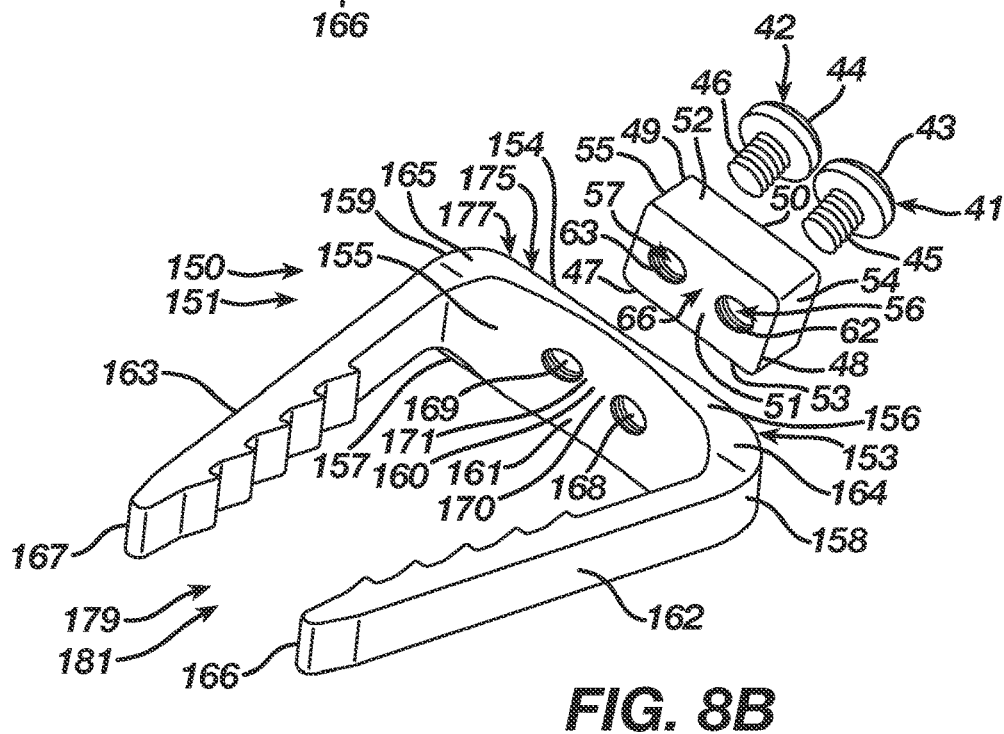
FIG. 8B is a bottom isometric view illustrating the orthopedic fixation system including the implant retainer disengaged from the orthopedic implant according to the sixth embodiment in the natural shape.
Figure 8C:
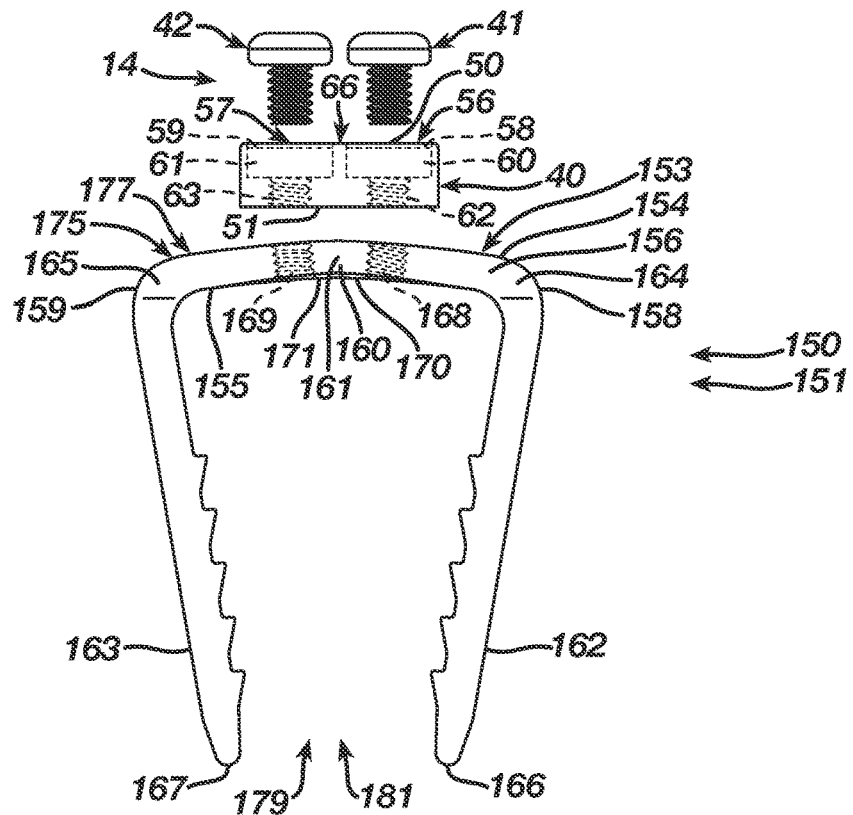
FIG. 8C is an elevation view illustrating the orthopedic fixation system including the implant retainer disengaged from the orthopedic implant according to the sixth embodiment in the natural shape.
Figure 8D:
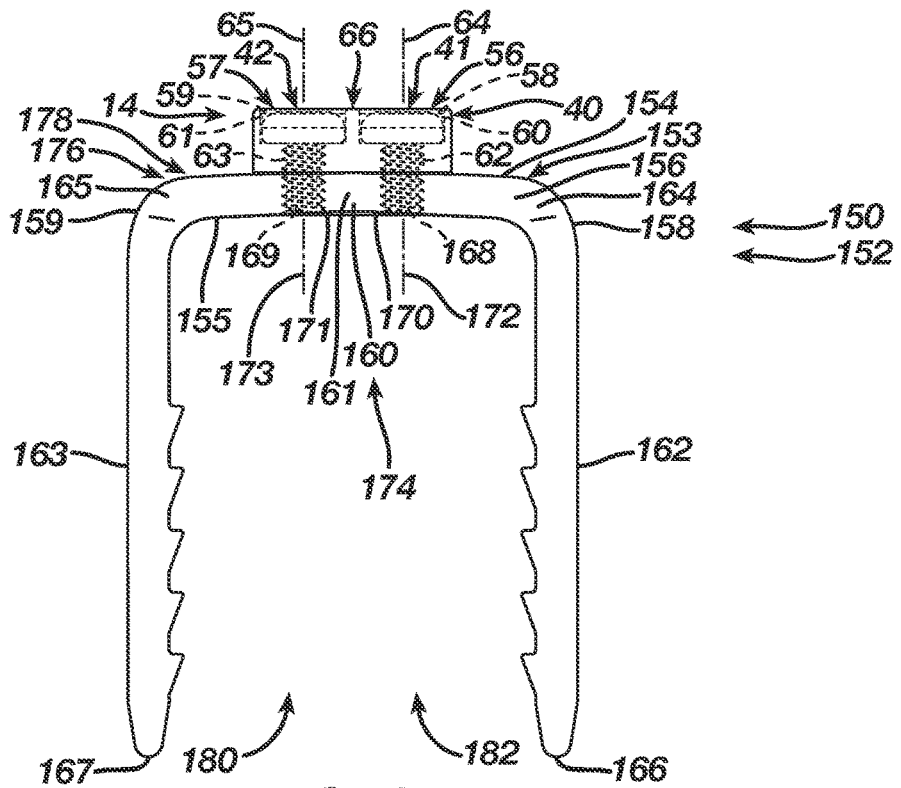
FIG. 8D is an elevation view illustrating the orthopedic fixation system including the implant retainer engaged with the orthopedic implant according to the sixth embodiment in an insertion shape.
Figure 9A:
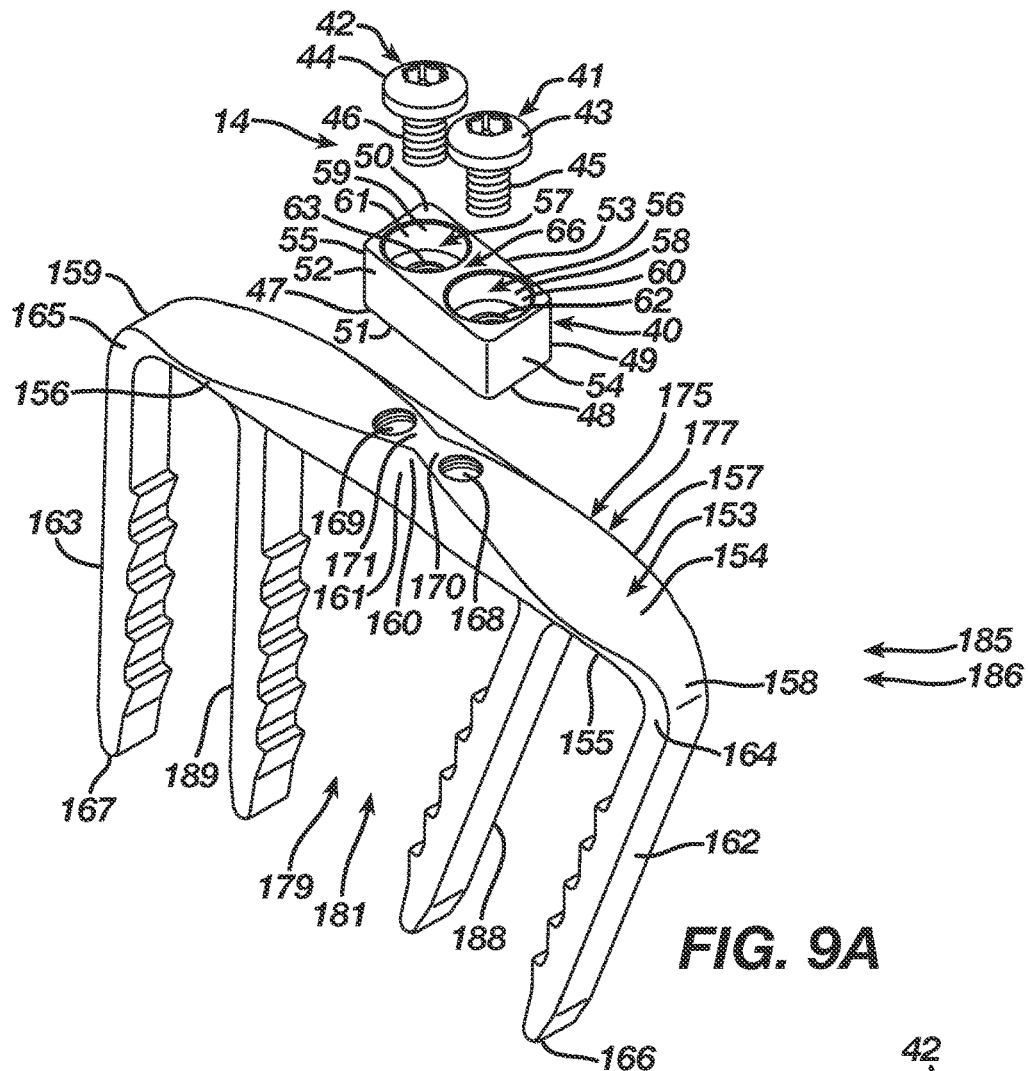
FIG. 9A is a top isometric view illustrating the orthopedic fixation system including the implant retainer disengaged from an orthopedic implant according to a seventh embodiment in a natural shape.
Figure 9B:
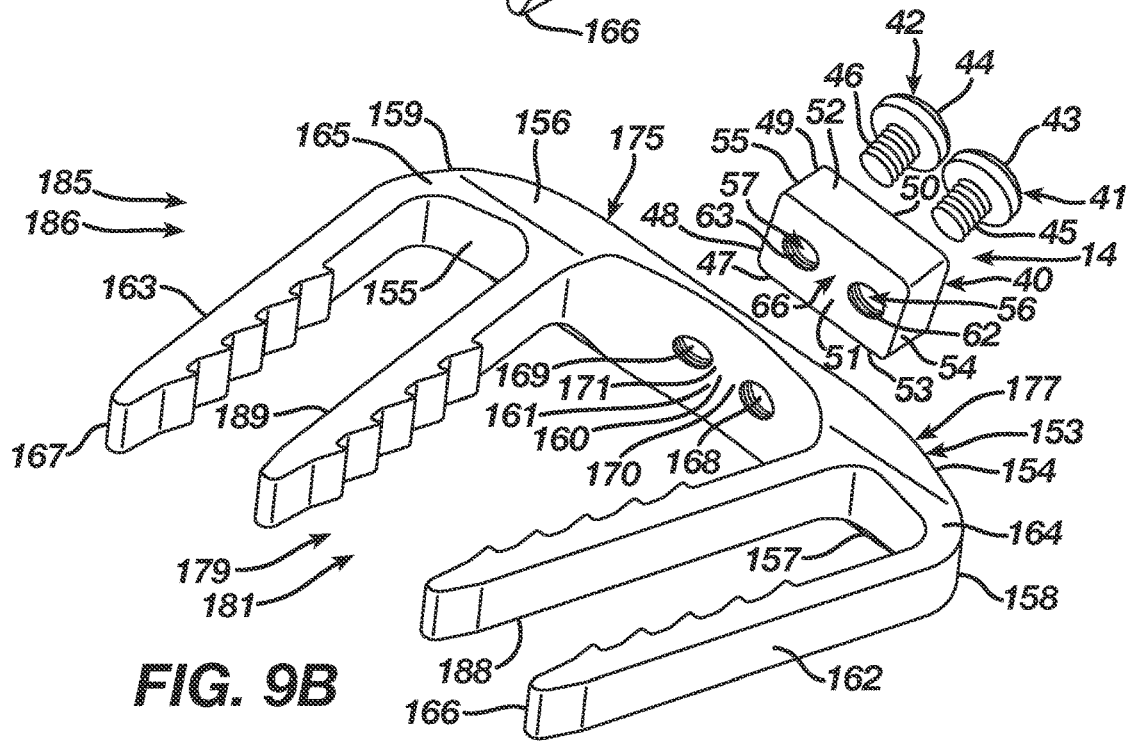
FIG. 9B is a bottom isometric view illustrating the orthopedic fixation system including the implant retainer disengaged from the orthopedic implant according to the seventh embodiment in the natural shape.
Figure 9C:
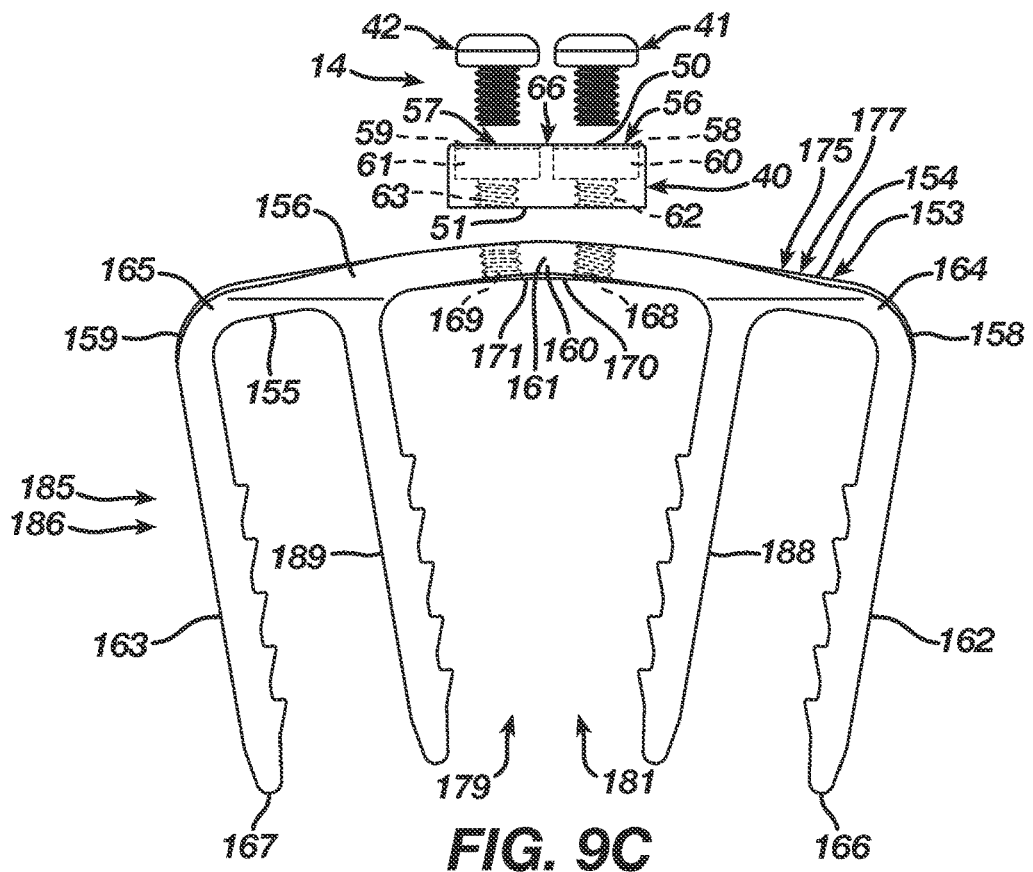
FIG. 9C is an elevation view illustrating the orthopedic fixation system including the implant retainer disengaged from the orthopedic implant according to the seventh embodiment in the natural shape.
Figure 9D:
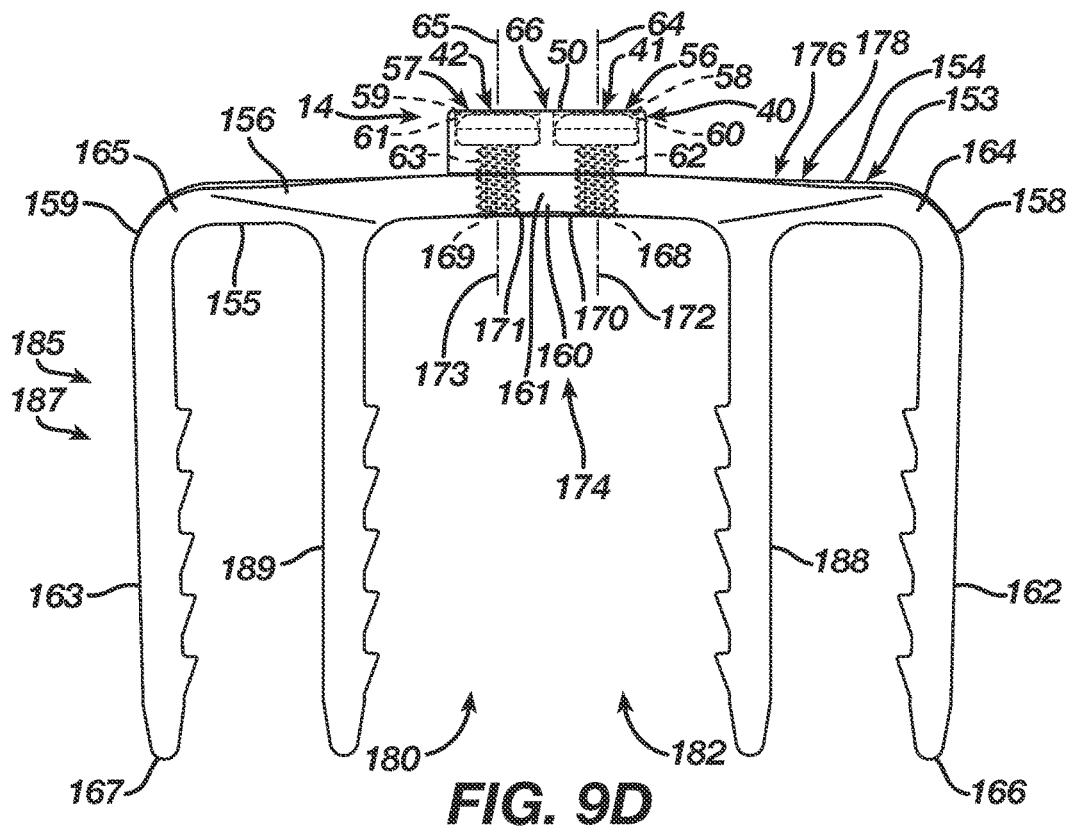
FIG. 9D is an elevation view illustrating the orthopedic fixation system including the implant retainer engaged with the orthopedic implant according to the seventh embodiment in an insertion shape.
Figure 10A:
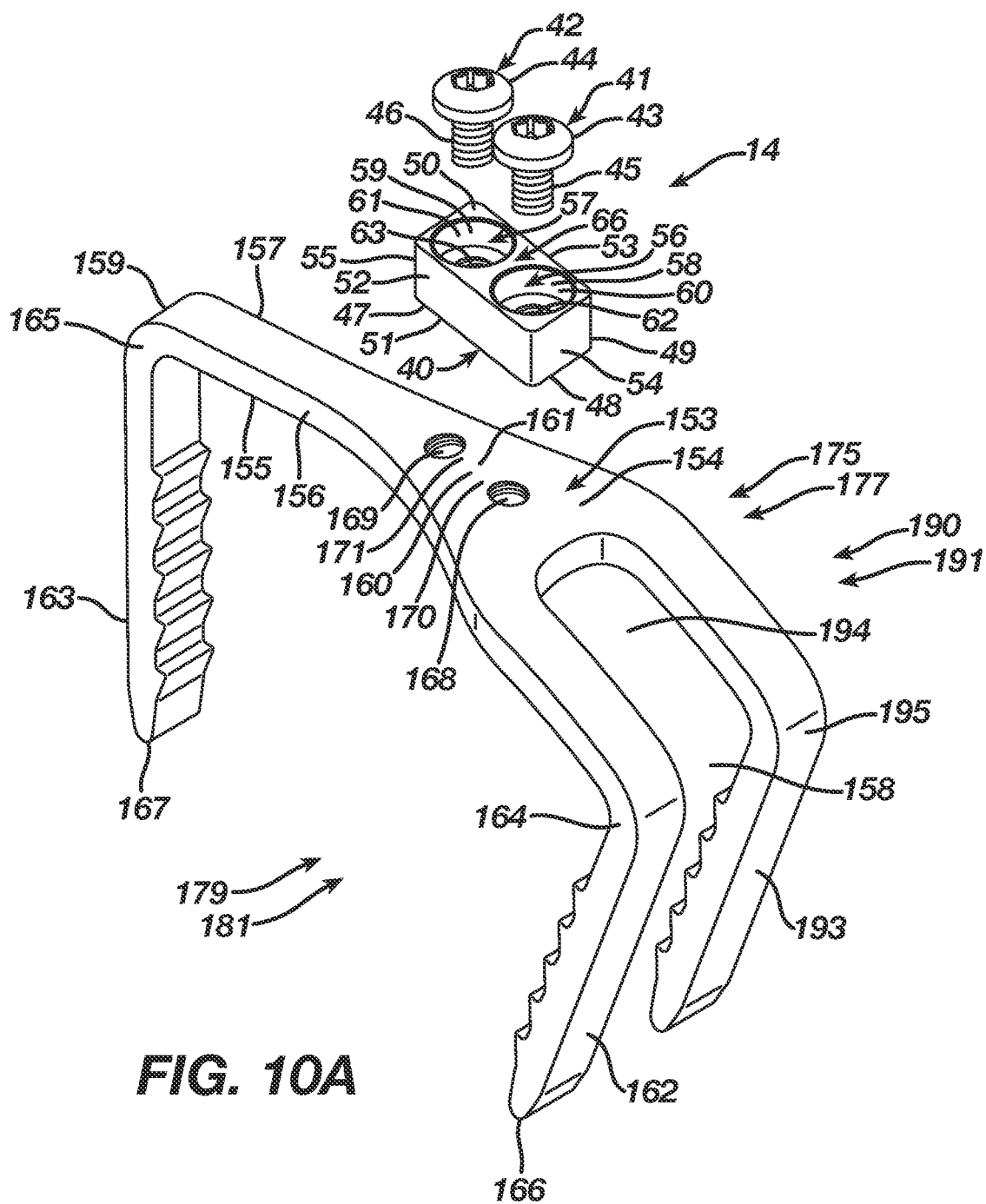
FIG. 10A is a top isometric view illustrating the orthopedic fixation system including the implant retainer disengaged from an orthopedic implant according to an eighth embodiment in a natural shape.
Figure 10B:
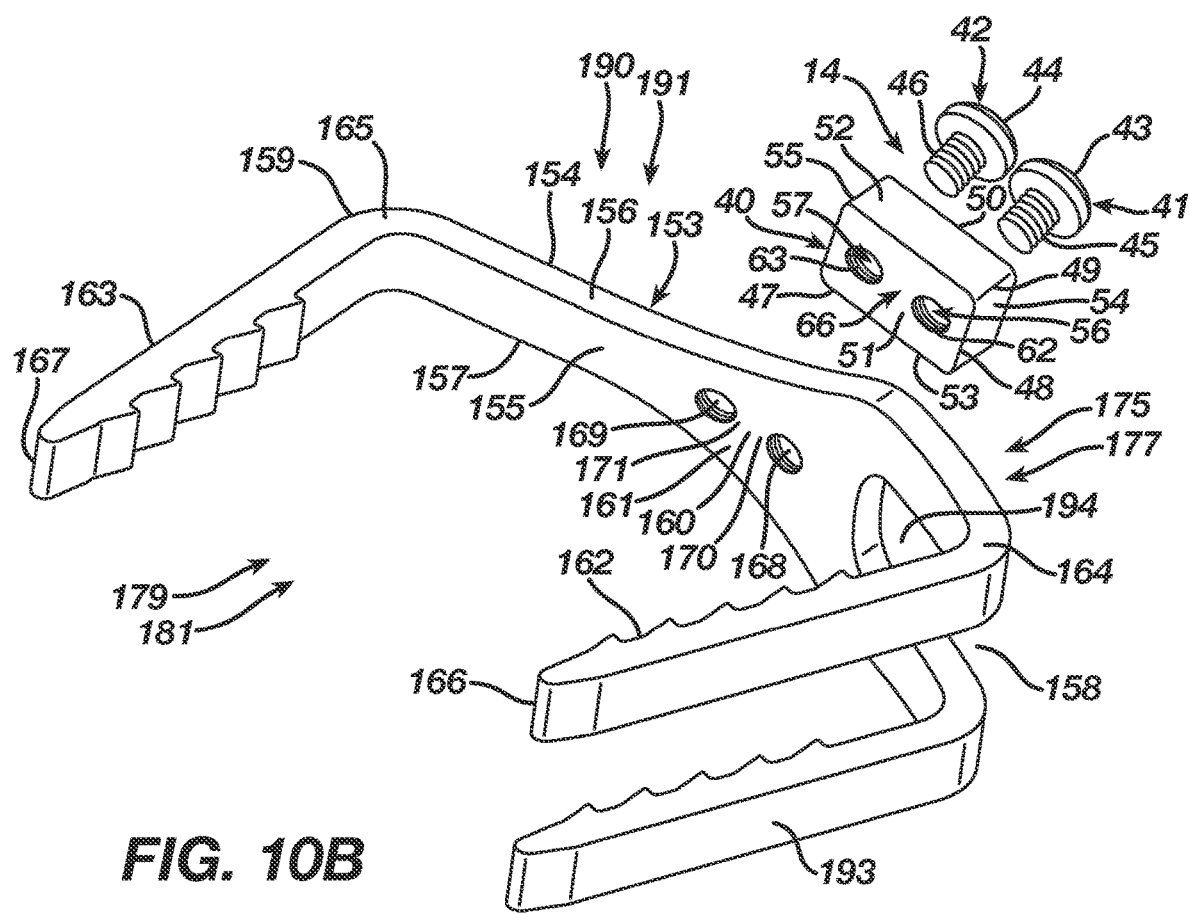
FIG. 10B is a bottom isometric view illustrating the orthopedic fixation system including the implant retainer disengaged from the orthopedic implant according to the eighth embodiment in the natural shape.
Figure 10C:
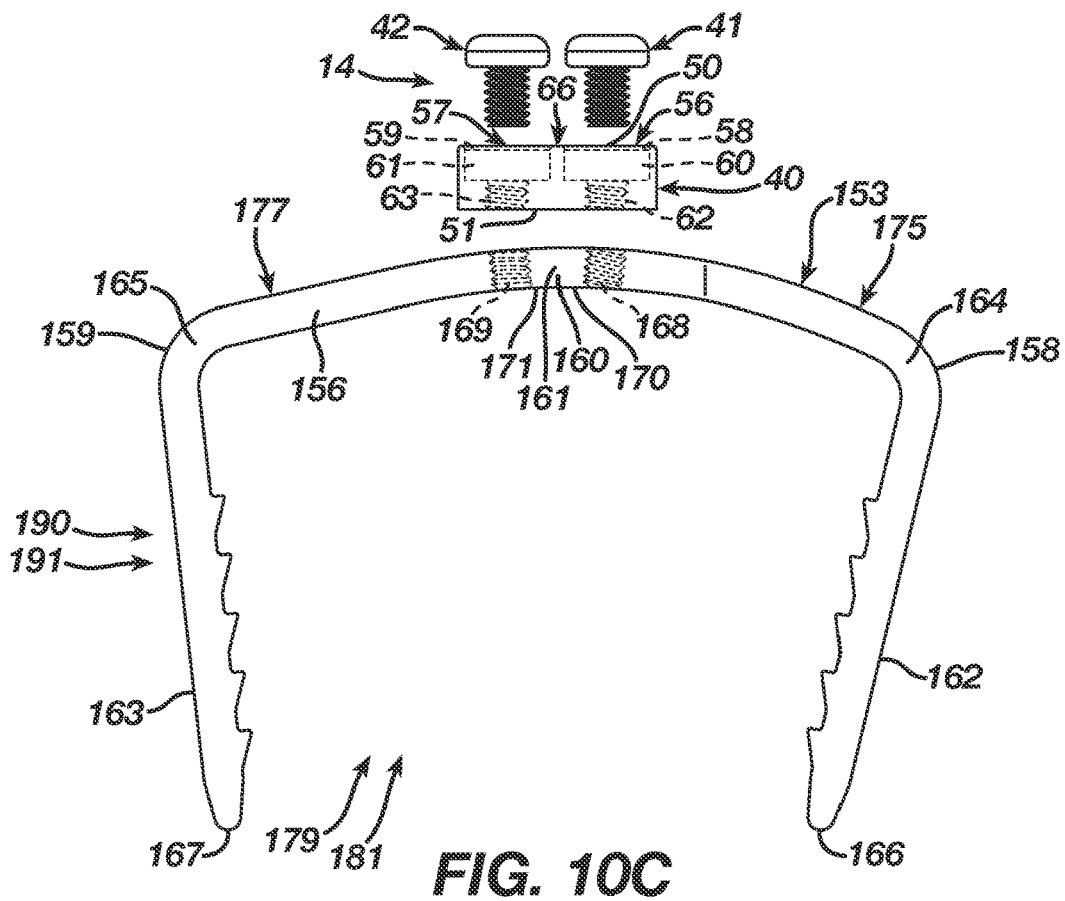
FIG. 10C is an elevation view illustrating the orthopedic fixation system including the implant retainer disengaged from the orthopedic implant according to the eighth embodiment in the natural shape.
Figure 10D:
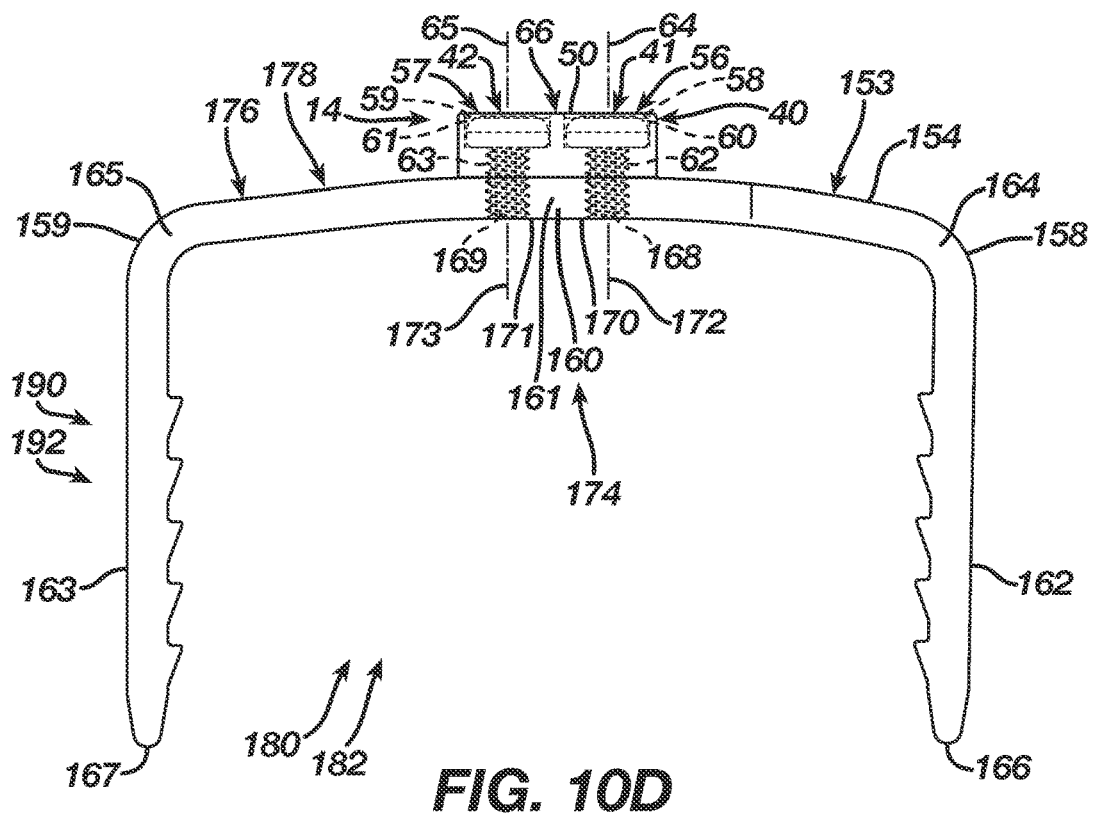
FIG. 10D is an elevation view illustrating the orthopedic fixation system including the implant retainer engaged with the orthopedic implant according to the eighth embodiment in an insertion shape.
Figure 11A:
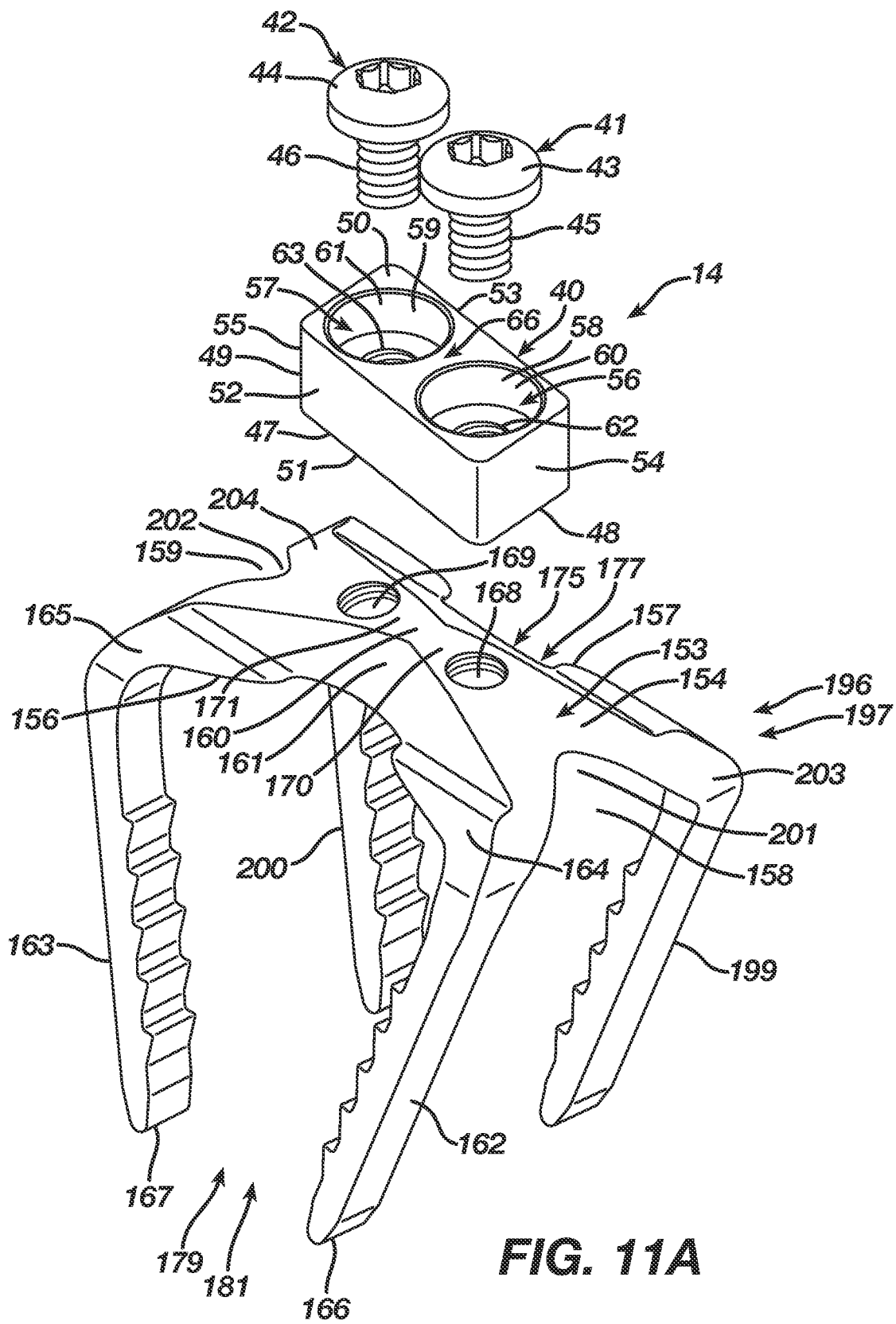
FIG. 11A is a top isometric view illustrating the orthopedic fixation system including the implant retainer disengaged from an orthopedic implant according to a ninth embodiment in a natural shape.
Figure 11B:
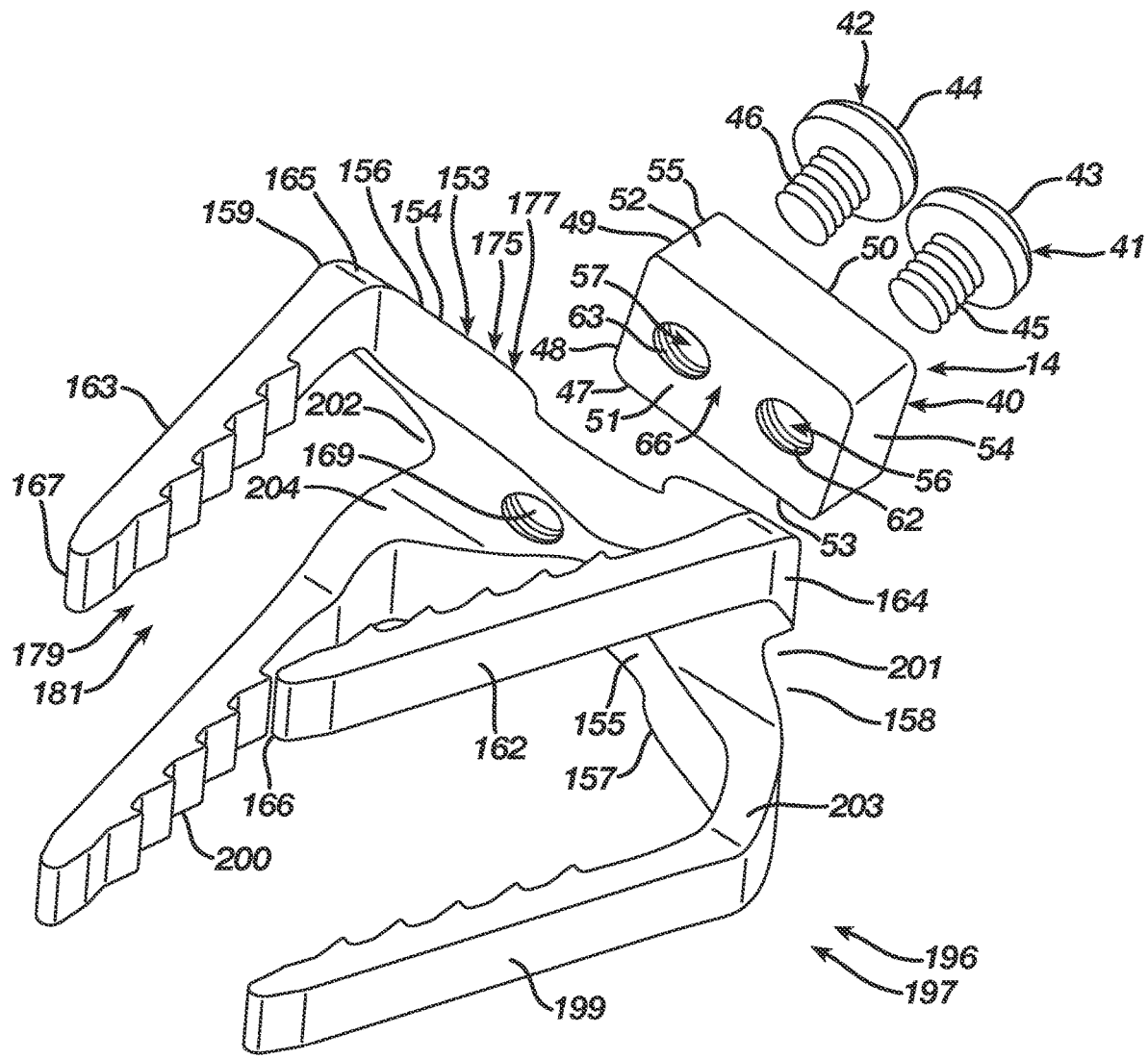
FIG. 11B is a bottom isometric view illustrating the orthopedic fixation system including the implant retainer disengaged from the orthopedic implant according to the ninth embodiment in the natural shape.
Figure 11C:
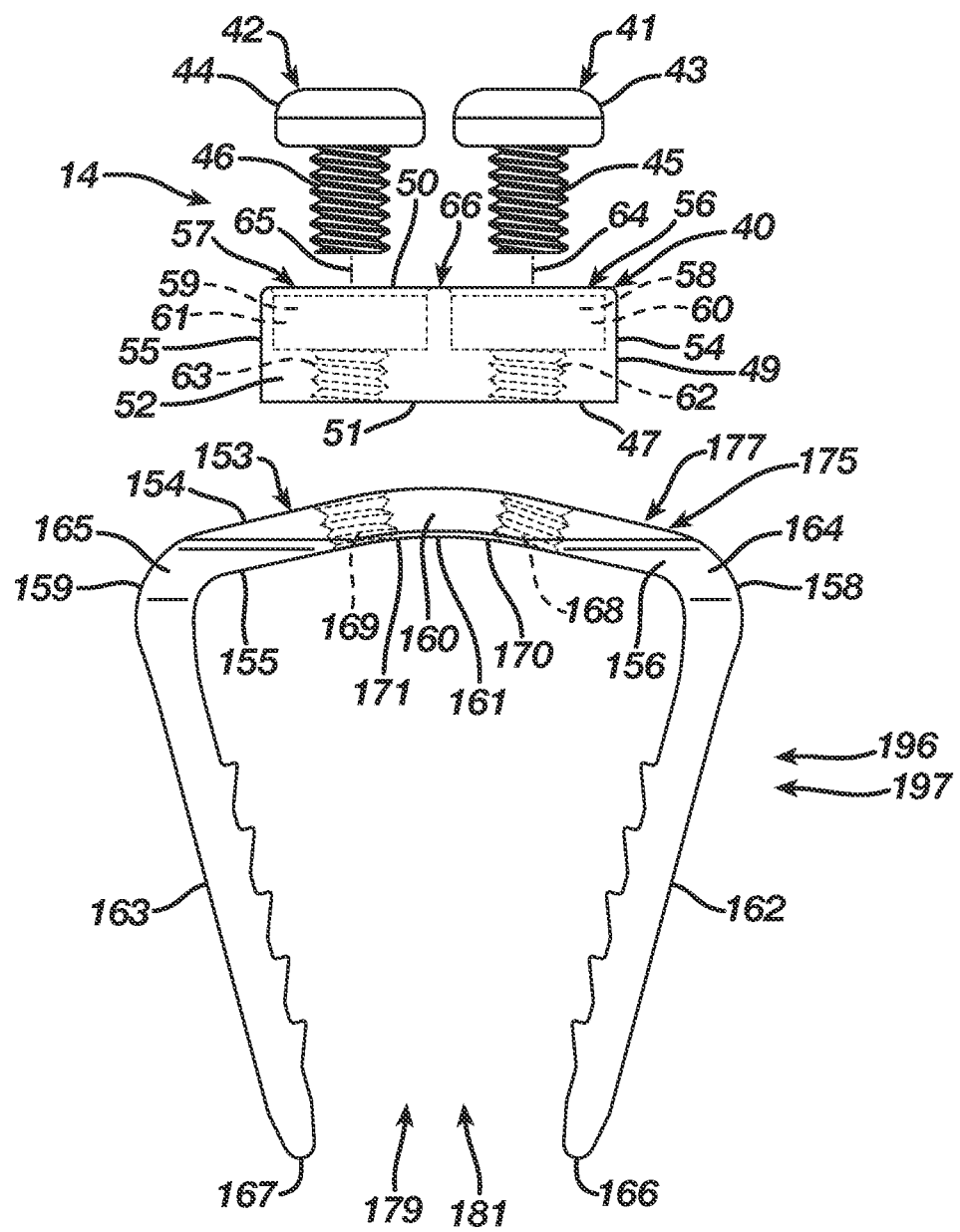
FIG. 11C is an elevation view illustrating the orthopedic fixation system including the implant retainer disengaged from the orthopedic implant according to the ninth embodiment in the natural shape.
Figure 11D:
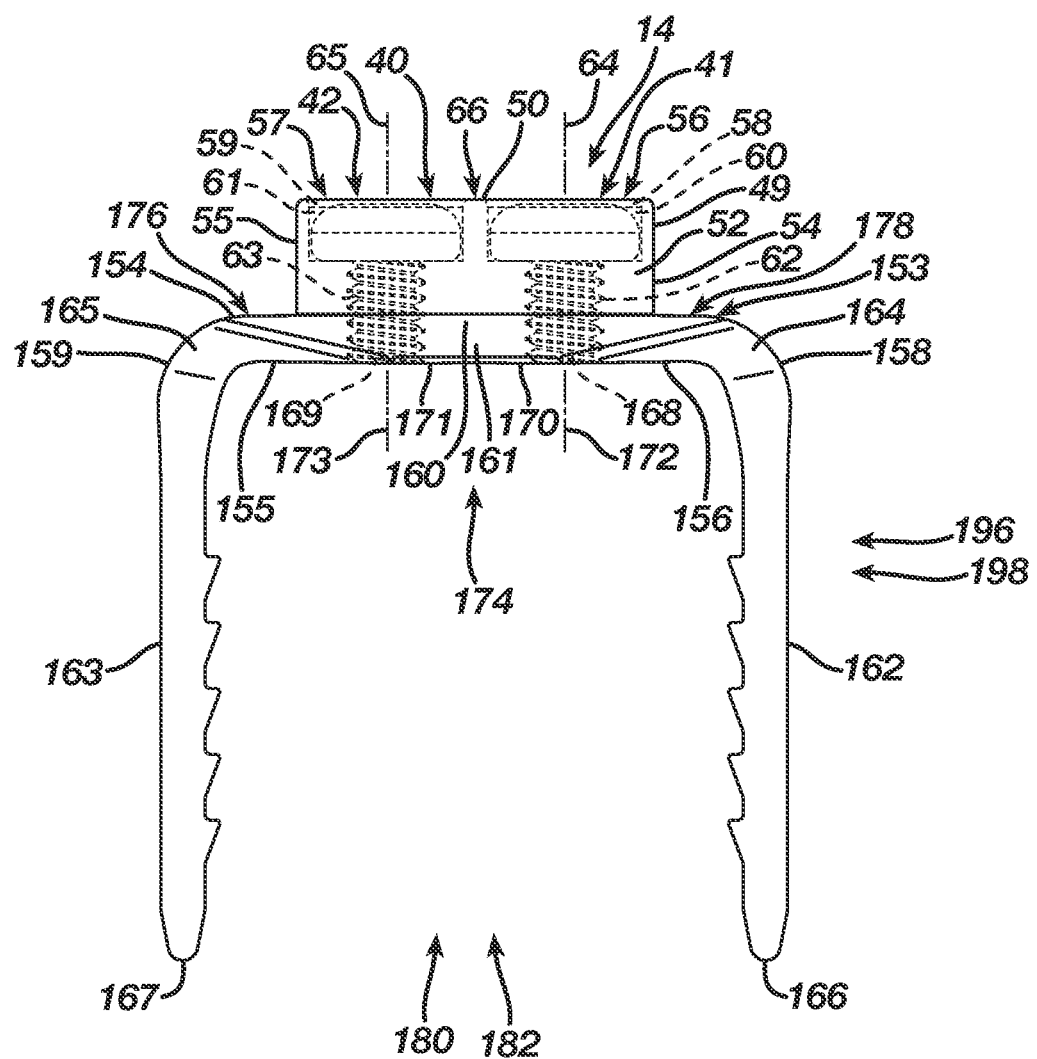
FIG. 11D is an elevation view illustrating the orthopedic fixation system including the implant retainer engaged with the orthopedic implant according to the ninth embodiment in an insertion shape.

FIGS. 8A-8C illustrate an orthopedic implant 150 according to a sixth embodiment in the natural shape 151, whereas FIG. 8D illustrates the orthopedic implant 150 in an insertion shape 152. The implant 150 in the sixth embodiment may be manufactured from a shape memory material with superelastic or temperature dependent properties (e.g., Nitinol) such that the implant 150 transitions between its natural shape 151 and its insertion shape 152. The implant 150 when deformed from its natural shape 151 to its insertion shape 152 stores energy deliverable to bone, bones, or bone pieces. In accordance with its manufacture from shape memory material, the implant 150 begins in its natural shape 151, is transitionable to its insertion shape 152, and, once implanted in bone, bones, or bone pieces, attempts to transition from its insertion shape 152 to its natural shape 151 whereby the implant 150 delivers the energy stored therein to the bone, bones, or bone pieces in order to affix the bone, bones, or bone pieces and promote a healing thereof. In the sixth embodiment, attempted transition of the implant 150 from its insertion shape 152 to its natural shape 151 continuously compresses the bone, bones, or bone pieces to promote fusion thereof.

The implant 150 includes a bridge 153 with upper and lower surfaces 154 and 155, first and second sides 156 and 157, and first and second ends 158 and 159. The implant 150 includes a transition section 160 located at a center section 161 of the implant 150 and thus the bridge 153. The implant 150 in the sixth embodiment includes an anchoring member in the form of a first leg 162 extending from the first end 158 of the implant 150 and thus the bridge 153 in order to provide the implant 150 and thus the bridge 153 with an anchoring segment 164. Likewise, the implant 150 includes an anchoring member in the form of a second leg 163 extending from the second end 159 of the implant 150 and thus the bridge 153 in order to provide the implant 150 and thus the bridge 153 with an anchoring segment 165. In the sixth embodiment, the first and second legs 162 and 163 are formed integrally with the implant 150 and thus the bridge 153 at respective first and second ends 158 and 159. Each leg 162 and 163, which has a respective tip 166 and 167, may include barbs thereon that improve the pull-out resistance of the implant 150. The implant 150 includes anchoring members in the form of the first and second legs 162 and 163 in order to facilitate a securing of the implant 150 with bone, bones, or bone pieces whereby the bridge 153 between the legs 162 and 163 traverses a fixation zone of the bone, bones, or bone pieces such that the implant 150, after its insertion and attempted transition from the insertion shape 152 to the natural shape 151, delivers energy to the bone, bones, or bone pieces at the fixation zone.

The implant 150, and thus the bridge 153, includes a first securing feature in the form of a first aperture 168, which is preferably threaded, extending therethrough from the upper surface 154 to the lower surface 155. The first aperture 168 preferably is located adjacent the transition section 160 at a first side 170 thereof. Similarly, the implant 150, and thus the bridge 153, includes a second securing feature in the form a second aperture 169, which is preferably threaded, extending therethrough from the upper surface 154 to the lower surface 155. The second aperture 169 preferably is located adjacent the transition section 150 at a second side 171 thereof. The first aperture 168 and the second aperture 169 provide engagement points for the implant retainer 14 with the implant 150. As such, the first aperture 168 at a vertical axis 172 and the second aperture 169 at a vertical axis 173, when the implant 150 resides in the insertion shape 152, are spaced apart across the transition section 160 a distance 174 that allows the first and second apertures 168 and 169 to facilitate a securing of the implant retainer 14 with the implant 150 at the transition section 160.

The regular inherent shape of the implant 150, as illustrated in FIGS. 8A-8C, is its natural shape 151 where the transition section 160 locates the bridge 153 in a natural form 175 consisting of a closed or angular profile whereby the first and second ends 158 and 159 reside at a first distance 177. Locating the bridge 153 in the natural form 175 places the first and second legs 162 and 163 in a natural position 179 whereby the first and second legs 162 and 163 are convergent and spaced apart at a first distance 181. Nevertheless, as illustrated in FIG. 8D, the implant 150 is deformable under the action of superelasticity or temperature dependent shape memory to its insertion shape 152 where the transition section 160 deforms to store energy while also moving the bridge 153 from its natural form 175 to an insertion form 176 which is an open or substantially linear profile whereby the first and second ends 158 and 159 reside at a second distance 178 that is greater than the first distance 177. Moving the bridge 153 to the insertion form 176 places the first and second legs 162 and 163 in an insertion position 180 whereby the first and second legs 162 and 163 are substantially parallel and spaced apart at a second distance 182 that is greater than the first distance 181. Since the insertion shape 152 is not the regular inherent shape of the implant 150, the bridge 153 typically is mechanically constrained using the implant retainer 14 whereby the implant retainer 14 maintains the bridge 153 in the insertion form 176 and thus the first and second legs 162 and 163 in the insertion position 180. In particular, the implant retainer 14 couples with the implant 150 via the first and second apertures 168 and 169, which are located at the distance 174 due to the implant 150 residing in the insertion shape 152, such that the implant retainer 14 holds the bridge 153 in the insertion form 176 and thus the first and second legs 162 and 163 in the insertion position 180, resulting in the implant retainer 14 constraining the deformed transition section 160 in order to maintain the implant 150 in its insertion shape 152. After implantation into bone, bones, or bone pieces and a release of the implant retainer 14, including, if necessary, a heating of the implant 150, the implant 150 delivers the energy stored in the transition section 160 whereby the bridge 153 attempts to transition from its insertion form 176 to its natural form 175 while the first and second legs 162 and 163 attempt to transition from their insertion position 180 to their natural position 179 such that the implant 150, which attempts transition from its insertion shape 152 to its natural shape 151, affixes the bone, bones, or bone pieces through an application of a compressive force thereto.

During formation of the orthopedic fixation system 10 through a securing of the implant retainer 14 with the implant 150 as illustrated in FIGS. 8A-8D, the implant 150 is mechanically deformed from the natural shape 151 to the insertion shape 152 such that the implant 150 stores mechanical energy. Mechanical deformation of the implant 150 may include cooling of the implant 150 whereby the implant 150 transitions from its austenite phase to its martensite phase in order to facilitate an easier mechanical deformation of the implant 150 from its natural shape 151 to its insertion shape 152 prior to a loading of the implant retainer 14 with the implant 150. Upon mechanical deformation of the implant 150 whereby the transition section 160 deforms to store energy while also moving the bridge 153 from its natural form 175 where the first and second ends 158 and 159 reside at the first distance 177 to its insertion form 178 where the first and second ends 158 and 159 reside at the second distance 178 and the first and second legs 162 and 163 from their natural position 179 where the first and second legs 162 and 163 reside at the first distance 181 to their insertion position 180 where the first and second legs 162 and 163 reside at the second distance 182, the first aperture 168 and the second aperture 169 due to the movement of the bridge 153 now are spaced apart across the transition section 160 the distance 174. With the bridge 153 in its insertion form 176 and the first and second apertures 168 and 169 residing at the distance 174, the retention block 40 seats atop the bridge 153 at the upper surface 154 thereof in abutting relationship with bridge 153 between the first and second sides 156 and 157 and the first and second ends 158 and 159 such that the first hole 56 and the second hole 57, which reside at the distance 66 equal to the distance 174, align respectively with the first aperture 168 and the second aperture 169. The first fastener 41 via a threading therein inserts into the first hole 56 until the head 43 seats in the counterbore 58 and the shaft 45 extends through the lower segment 62 and into the first aperture 168 to a position whereby the shaft 45 resides at the lower surface 155 of the bridge 153 without protruding therefrom. Similarly, the second fastener 42 via a threading therein inserts into the second hole 57 until the head 44 seats in the counterbore 59 and the shaft 46 extends through the lower segment 63 and into the second aperture 169 to a position whereby the shaft 46 resides at the lower surface 155 of the bridge 153 without protruding therefrom. The engagement of the first fastener 41 with both the first hole 56 of the retention block 40 and the first aperture 168 of the bridge 153 and the second fastener 42 with both the second hole 57 of the retention block 40 and the second aperture 169 of the bridge 153 secures the retention block 40 with the bridge 153 across the transition section 160 whereby the retention block 40, which spans the transition section 160, mechanically constrains the bridge 153 and thus the implant 150 in order to hold the bridge 153 in the insertion form 176, the first and second legs 162 and 163 in the insertion position 180, and the implant 110 in the insertion shape 112 and prevent a transition of the bridge 153 from the insertion form 176 to the natural form 175, the first and second legs 162 and 163 from the insertion position 180 to the natural position 179, and the implant 150 from the insertion shape 152 to the natural shape 151.

In accordance with the orthopedic fixation system 10, the implant retainer 14, when loaded with the implant 150 in that the implant retainer 14 secures atop the bridge 153 as previously described, retains the implant 150 in its insertion shape 152 such that the implant 150 is ready for securing with bone, bones, or bone pieces, and, in particular, into a first bone and a second bone, which are presented herein as an example. A surgeon aligns the first bone with the second bone at a fusion zone in an orientation that promotes fixation of the first bone with the second bone and a proper healing thereof. The surgeon then drills a drill hole in the first bone and a drill hole in the second bone. The drill holes are drilled at spacings and locations desired for insertion of the first leg 162 into the first bone and the second leg 163 into the second bone whereby the bridge 153 of the implant 150 when the implant 150 resides in its insertion shape 152 spans the fusion zone with the transition section 160 located at the fusion zone. While not required, the surgeon may create grooves in the first and second bones that facilitate a more flush seating of the bridge 153 for the implant 150 relative to the first and second bones. The surgeon next positions the tip 166 of the first leg 162 for the implant 150 adjacent the pre-drilled hole of the first bone and the tip 167 of the second leg 163 for the implant 150 adjacent the pre-drilled hole of the second bone. After the tips 166 and 167 reside respectively at the pre-drilled holes of the first and second bones, the surgeon inserts the first and second legs 162 and 163 respectively into the pre-drilled holes until the bridge 153 abuts the first bone and the second bone with the transition section 160 located at the fusion zone. While an insertion of the implant 150 typically includes pre-drilling of the holes in the first and second bones, the surgeon may impact the first and second legs 162 and 163 respectively into the first and second bones at a desired location.

After affixing the implant 150 with the first and second bones through the insertion of the first and second legs 162 and 163 respectively into the pre-drilled holes whereby the bridge 153 spans the first bone and the second bone with its transition section 160 located at the fusion zone, the surgeon removes the first fastener 41 from the first aperture 168 of the implant 150 and if desired from the first hole 56 of the retention block 40 and the second fastener 42 from the second aperture 169 of the implant 150 and if desired from the second hole 57 of the retention block 40. With the fasteners 41 and 42 removed from engagement with the implant 150 and if desired from the retention block 40, the retention block 40 releases the implant 150, allowing the surgeon to remove the retention block 40 from atop the implant 150. The implant 150, which is completely released from the implant retainer 14, attempts transition from its insertion shape 152 to its natural shape 151 whereby the implant 150 delivers the energy stored in its transition section 160 to the first bone and the second bone, resulting in the implant 150 affixing the first bone and the second bone through an application of a compressive force to the fixation zone. The implant retainer 14 accordingly improves insertion of the implant 150 because the implant retainer 14 permits seating of the implant 150 without the necessity of tamping the implant 150 flush with the first and the second bones after a release of the implant 150 from the implant retainer 14. Moreover, the implant retainer 14 does not release its constraint of the implant 150 until the implant 150 is completely affixed to the first and second bones with its transition section 160 located across the fusion zone thereof such that the implant retainer 14 prevents the implant 150 from prematurely delivering the energy stored therein to the first and second bones at the fixation zone thereof.

The orthopedic fixation system 10 as illustrated in FIGS. 9A-9D includes the implant retainer 14 and an orthopedic implant 185 according to a seventh embodiment transitionable between a natural shape 186 and an insertion shape 187. The implant 185 is substantially similar in design and operation relative to the implant 150 according to the sixth embodiment such that, for the sake of brevity, only differences therebetween will be described herein. Moreover, one of ordinary skill in the art will recognize that like parts of the implant 185 labeled with like numerals of the implant 150 incorporate a design and function as previously set forth in the detailed description of the implant 150 according to the sixth embodiment. The implant 150 includes the first leg 162 at the first end 158 and the second leg 163 at the second end 159, whereas the implant 185 in addition to the first leg 162 and the second leg 163 includes a third leg 188 extending from the bridge 153 between the first end 158 and the center section 161 and a fourth leg 189 extending from the bridge 153 between the second end 159 and the center section 161 in order to more securely affix the implant 185 to bone, bones, or bone pieces. The implant retainer 14 engages the implant 185 according to the seventh embodiment and constrains the implant 185 in the insertion shape 187 substantially, completely identical to the implant 150 according to the sixth embodiment. Securing the implant 185 to bone, bones, or bone pieces for affixation thereof is substantially similar to the implant 150 as previously described, except the implant 185 includes insertion of the third and fourth legs 188 and 189 into bone, bones, or bone pieces in addition to the first and second legs 162 and 163. The implant retainer 14 releases the implant 185 according to the seventh embodiment for attempted transition from the insertion shape 187 to the natural shape 186 substantially, completely identical to the implant 150 according to the sixth embodiment.

The orthopedic fixation system 10 as illustrated in FIGS. 10A-10D includes the implant retainer 14 and an orthopedic implant 190 according to an eighth embodiment transitionable between a natural shape 191 and an insertion shape 192. The implant 190 is substantially similar in design and operation relative to the implant 150 according to the sixth embodiment such that, for the sake of brevity, only differences therebetween will be described herein. Moreover, one of ordinary skill in the art will recognize that like parts of the implant 190 labeled with like numerals of the implant 150 incorporate a design and function as previously set forth in the detailed description of the implant 150 according to the sixth embodiment. While the implant 190 is substantially similar in design and operation relative to the implant 150 according to the sixth embodiment, the implant 190 includes a Y-shaped configuration that facilitates affixation of the implant 190 with different sized and shaped bone, bones, or bone pieces. More particularly, the implant 150 includes the first leg 162 at the first end 158 and the second leg 163 at the second end 159, whereas the implant 190 in addition to the first leg 162 and the second leg 163 includes a third leg 193 extending from the bridge 153 whereby the first leg 162 and the third leg 193 are aligned and located adjacent at the first end 158 of the bridge 153. In the eighth embodiment, the implant 190, and thus the bridge 153, at the first end 158 divides via a cut-out 194 into the first anchoring segment 164 with the first leg 162 extending therefrom and a third anchoring segment 195 with the third leg 193 extending therefrom, thereby producing a Y-shaped configuration for the implant 190.

The implant retainer 14 engages the implant 190 according to the eighth embodiment and constrains the implant 190 in the insertion shape 192 substantially, completely identical to the implant 150 according to the sixth embodiment. Securing the implant 190 to bone, bones, or bone pieces for affixation thereof is substantially similar to the implant 150 as previously described, except the implant 190 includes insertion of the third leg 193 into bone, bones, or bone pieces in addition to the first and second legs 162 and 163. The implant retainer 14 releases the implant 190 according to the eighth embodiment for attempted transition from the insertion shape 192 to the natural shape 191 substantially, completely identical to the implant 150 according to the sixth embodiment.

The orthopedic fixation system 10 as illustrated in FIGS. 11A-11D includes the implant retainer 14 and an orthopedic implant 196 according to a ninth embodiment transitionable between a natural shape 197 and an insertion shape 198. The implant 196 is substantially similar in design and operation relative to the implant 150 according to the sixth embodiment such that, for the sake of brevity, only differences therebetween will be described herein. Moreover, one of ordinary skill in the art will recognize that like parts of the implant 196 labeled with like numerals of the implant 150 incorporate a design and function as previously set forth in the detailed description of the implant 150 according to the sixth embodiment. While the implant 196 is substantially similar in design and operation relative to the implant 150 according to the sixth embodiment, the implant 196 includes an H-shaped configuration that facilitates affixation of the implant 196 with different sized and shaped bone, bones, or bone pieces. More particularly, the implant 150 includes the first leg 162 at the first end 158 and the second leg 163 at the second end 159, whereas the implant 196 in addition to the first leg 162 and the second leg 163 includes a third leg 199 and a fourth leg 200 extending from the bridge 153 whereby the first leg 162 and the third leg 199 are aligned and located adjacent at the first end 158 of the bridge 153 and the second leg 163 and the fourth leg 200 are aligned and located adjacent at the second end 159 of the bridge 153. In the eighth embodiment, the implant 196, and thus the bridge 153, at the first end 158 divides via a cut-out 201 into the first anchoring segment 164 with the first leg 162 extending therefrom and a third anchoring segment 203 with the third leg 199 extending therefrom, thereby producing an H-shaped configuration for the implant 196. Likewise, the implant 196, and thus the bridge 153, at the second end 159 divides via a cut-out 202 into the second anchoring segment 165 with the second leg 163 extending therefrom and a fourth anchoring segment 204 with the fourth leg 200 extending therefrom, thereby producing an H-shaped configuration for the implant 196.

The implant retainer 14 engages the implant 191 according to the ninth embodiment and constrains the implant 191 in the insertion shape 198 substantially, completely identical to the implant 150 according to the sixth embodiment. Securing the implant 196 to bone, bones, or bone pieces for affixation thereof is substantially similar to the implant 150 as previously described, except the implant 196 includes insertion of the third leg 199 and fourth leg 200 into bone, bones, or bone pieces in addition to the first and second legs 162 and 163. The implant retainer 14 releases the implant 196 according to the ninth embodiment for attempted transition from the insertion shape 198 to the natural shape 197 substantially, completely identical to the implant 150 according to the sixth embodiment.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system, comprising:
    an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy, the orthopedic implant, comprising:
  a bridge with a first end and a second end,
  a transition section disposed in the bridge, whereby the transition section deforms to move the orthopedic implant between the natural shape and the insertion shape,
  a first anchoring segment disposed at the first end of the bridge,
  a second anchoring segment disposed at the second end of the bridge,
  a first aperture extending through the bridge adjacent the transition section at a first side thereof, and
  a second aperture extending through the bridge adjacent the transition section at a second side thereof; and
an implant retainer, configured to constrain the orthopedic implant in the insertion shape thereby preventing a transition of the orthopedic implant from the insertion shape to the natural shape, the implant retainer, comprising:
a first fastener,
a second fastener,
a retention block including a length between first and second ends thereof whereby the retention block fits atop the bridge of the orthopedic implant between the first and second anchoring segments of the orthopedic implant with the first end of the retention block interior of the first anchoring segment of the orthopedic implant and the second end of the retention block interior of the second anchoring segment of the orthopedic implant,
the retention block including a first hole therethrough adopted to receive the first fastener and a second hole therethrough adopted to receive the second fastener, the first hole and the second hole being spaced apart at a distance equal to the distance between the first aperture of the orthopedic implant and the second aperture of the orthopedic implant when the orthopedic implant resides in the insertion shape, and
the retention block, upon transition of the orthopedic implant from the natural shape to the insertion shape, being configured to span the transition section of the bridge when seated atop the bridge with the first hole of the retention block aligned with the first aperture of the bridge and the second hole of the retention block aligned with the second aperture of the bridge, whereby the first fastener inserts into the first hole of the retention block and extends into the first aperture and the second fastener inserts into the second hole of the retention block and extends into the second aperture thereby securing the retention block with the bridge across the transition section thereof, further whereby the retention block constrains the bridge and holds the orthopedic implant in the insertion shape thereby preventing a transition of the orthopedic implant from the insertion shape to the natural shape.

2. The orthopedic fixation system of claim 1, wherein:
the first aperture being configured for mechanical engagement with the first fastener thereby facilitating a rigid securing of the retention block with the bridge; and
the second aperture being configured for mechanical engagement with the second fastener thereby facilitating a rigid securing of the retention block with the bridge.

3. The orthopedic fixation system of claim 1, wherein:
the first hole including an upper segment with a counterbore configured to receive therein a head of the first fastener and a lower segment configured for mechanical engagement with a shaft of the first fastener; and
the second hole including an upper segment with a counterbore configured to receive therein a head of the second fastener and a lower segment configured for mechanical engagement with a shaft of the second fastener.

4. The orthopedic fixation system of claim 1, the orthopedic implant, comprising:
the first anchoring segment comprising a first opening extending through the bridge at the first end thereof, the first opening adapted to receive a screw therethrough; and
the second anchoring segment comprising a second opening extending through the bridge at the second end thereof, the second opening adapted to receive a screw therethrough.

5. The orthopedic fixation system of claim 4, the orthopedic implant, comprising:
the first anchoring segment comprising a third opening extending through the bridge at the first end thereof exterior of the first opening, the third opening adapted to receive a screw therethrough; and
the second anchoring segment comprising a fourth opening extending through the bridge at the second end thereof exterior of the second opening, the fourth opening adapted to receive a screw therethrough.

6. The orthopedic fixation system of claim 4, the orthopedic implant, comprising a third anchoring segment disposed at the first end of the bridge adjacent the first anchoring segment, the third anchoring segment comprising a third opening extending through the bridge at the first end thereof adjacent the first opening, the third opening adapted to receive a screw therethrough.

7. The orthopedic fixation system of claim 6, the orthopedic implant, comprising a fourth anchoring segment disposed at the second end of the bridge adjacent the second anchoring segment, the fourth anchoring segment comprising a fourth opening extending through the bridge at the second end thereof adjacent the second opening, the fourth opening adapted to receive a screw therethrough.

8. The orthopedic fixation system of claim 1, the orthopedic implant, comprising:
the first anchoring segment comprising a first leg extending from the bridge at the first end thereof; and
the second anchoring segment comprising a second leg extending from the bridge at the second end thereof.

9. The orthopedic fixation system of claim 8, the orthopedic implant, comprising:
the first anchoring segment comprising a third leg extending from the bridge interior of the first leg; and
the second anchoring segment comprising a fourth leg extending from the bridge interior of the second leg.

10. The orthopedic fixation system of claim 8, the orthopedic implant, comprising a third anchoring segment disposed at the first end of the bridge adjacent the first anchoring segment, the third anchoring segment comprising a third leg extending from the bridge at the first end thereof adjacent the first leg.

11. The orthopedic fixation system of claim 10, the orthopedic implant, comprising a fourth anchoring segment disposed at the second end of the bridge adjacent the second anchoring segment, the fourth anchoring segment comprising a fourth leg extending from the bridge at the second end thereof adjacent the second leg.

12. An orthopedic fixation system, comprising:
an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy, the orthopedic implant, comprising:
a bridge with a first end and a second end,
a transition section disposed in the bridge, whereby the transition section deforms to move the orthopedic implant between the natural shape and the insertion shape,
a first opening extending through the bridge at the first end thereof, the first opening configured to receive a bone screw therethrough,
a second opening extending through the bridge at the second end thereof, the first opening configured to receive a bone screw therethrough,
a first aperture extending through the bridge adjacent the transition section at a first side thereof, the first aperture configured to receive a fastening screw therein, and
a second aperture extending through the bridge adjacent the transition section at a second side thereof, the second aperture configured to receive a fastening screw therein, the first aperture and the second aperture, upon transition of the orthopedic implant from the natural shape to the insertion shape, being spaced apart across the transition section a distance; and
an implant retainer configured to engage the orthopedic implant and constrain the orthopedic implant in the insertion shape, the implant retainer, comprising:
a first fastening screw,
a second fastening screw,
a retention block including a length between first and second ends thereof whereby the retention block fits atop the bridge of the orthopedic implant between the first and second openings of the orthopedic implant with the first end of the retention block interior of the first opening of the orthopedic implant and the second end of the retention block interior of the second opening of the orthopedic implant,
the retention block including a first hole therethrough adapted to receive the first fastening screw and a second hole therethrough adapted to receive the second fastening screw, the first hole and the second hole being spaced apart at a distance equal to the distance between the first aperture of the orthopedic implant and the second aperture of the orthopedic implant when the orthopedic implant resides in the insertion shape, and
the retention block, upon transition of the orthopedic implant from the natural shape to the insertion shape, being configured to span the transition section of the bridge when seated atop the bridge with the first hole of the retention block aligned with the first aperture of the bridge and the second hole of the retention block aligned with the second aperture of the bridge, whereby the first fastening screw inserts into the first hole of the retention block and extends into the first aperture and the second fastening screw inserts into the second hole of the retention block and extends into the second aperture thereby securing the retention block with the bridge across the transition section thereof, further whereby the retention block constrains the bridge and holds the orthopedic implant in the insertion shape thereby preventing a transition of the orthopedic implant from the insertion shape to the natural shape.

13. The orthopedic fixation system of claim 12, wherein:
the first aperture being configured for mechanical engagement with the first fastening screw thereby facilitating a rigid securing of the retention block with the bridge; and
the second aperture being configured for mechanical engagement with the second fastening screw thereby facilitating a rigid securing of the retention block with the bridge.

14. The orthopedic fixation system of claim 12, wherein:
the first hole including an upper segment with a counterbore configured to receive therein a head of the first fastening screw and a lower segment configured for mechanical engagement with a shaft of the first fastening screw; and
the second hole including an upper segment with a counterbore configured to receive therein a head of the second fastening screw and a lower segment configured for mechanical engagement with a shaft of the second fastening screw.

15. The orthopedic fixation system of claim 12 the orthopedic implant, comprising:
a third opening extending through the bridge at the first end thereof exterior of the first opening, the third opening adapted to receive a screw therethrough; and
a fourth opening extending through the bridge at the second end thereof exterior of the second opening, the fourth opening adapted to receive a screw therethrough.

16. The orthopedic fixation system of claim 12, the orthopedic implant, comprising a third opening extending through the bridge at the first end thereof adjacent the first opening, the third opening adapted to receive a screw therethrough.

17. The orthopedic fixation system of claim 16, the orthopedic implant, comprising a fourth opening extending through the bridge at the second end thereof adjacent the second opening, the fourth opening adapted to receive a screw therethrough.

18. An orthopedic fixation system, comprising:
an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy, the orthopedic implant, comprising:
a bridge with a first end and a second end,
a transition section disposed in the bridge, whereby the transition section deforms to move the orthopedic implant between the natural shape and the insertion shape,
a first leg extending from the bridge at the first end thereof,
a second leg extending from the bridge at the second end thereof,
a first aperture extending through the bridge adjacent the transition section at a first side thereof, and
a second aperture extending through the bridge adjacent the transition section at a second side thereof, the first aperture and the second aperture, upon transition of the orthopedic implant from the natural shape to the insertion shape, being spaced apart across the transition section a distance; and an implant retainer configured to engage the orthopedic implant and constrain the orthopedic implant in the insertion shape, the implant retainer, comprising:
a first fastener,
a second fastener,
a retention block including a first hole therethrough adapted to receive the first fastener and a second hole therethrough adapted to receive the second fastener, the first hole and the second hole being spaced apart a distance equal to the distance between the first aperture of the bridge and the second aperture of the orthopedic implant when the orthopedic implant resides in the insertion shape, and
the retention block, upon transition of the orthopedic implant from the natural shape to the insertion shape, being configured to span the transition section of the bridge when seated atop the bridge with the first hole of the retention block aligned with the first aperture of the bridge and the second hole of the retention block aligned with the second aperture of the bridge, whereby the first fastener inserts into the first hole of the retention block and extends into the first aperture and the second fastener inserts into the second hole of the retention block and extends into the second aperture thereby securing the retention block with the bridge across the transition section thereof, further whereby the retention block constrains the bridge and holds the orthopedic implant in the insertion shape thereby preventing a transition of the orthopedic implant from the insertion shape to the natural shape.

19. The orthopedic fixation system of claim 18, wherein:
the first aperture being configured for mechanical engagement with the first fastener thereby facilitating a rigid securing of the retention block with the bridge; and
the second aperture being configured for mechanical engagement with the second fastener thereby facilitating a rigid securing of the retention block with the bridge.

20. The orthopedic fixation system of claim 18, wherein:
the first hole including an upper segment with a counterbore configured to receive therein a head of the first fastener and a lower segment configured for mechanical engagement with a shaft of the first fastener; and
the second hole including an upper segment with a counterbore configured to receive therein a head of the second fastener and a lower segment configured for mechanical engagement with a shaft of the second fastener.

21. The orthopedic fixation system of claim 18, the orthopedic implant, comprising:
a third leg extending from the bridge interior of the first leg; and
a fourth leg extending from the bridge interior of the second leg.

22. The orthopedic fixation system of claim 18, the orthopedic implant, comprising a third leg extending from the bridge at the first end thereof adjacent the first leg.

23. The orthopedic fixation system of claim 22, the orthopedic implant, comprising a fourth leg extending from the bridge at the second end thereof adjacent the second leg.

* * * * *